US007511075B2

(12) United States Patent
Dugan et al.

(10) Patent No.: US 7,511,075 B2
(45) Date of Patent: Mar. 31, 2009

(54) THERAPEUTIC MALONIC ACID/ACETIC ACID $C_{60}$ TRI-ADDUCTS OF BUCKMINSTERFULLERENE AND METHODS RELATED THERETO

(75) Inventors: Laura L Dugan, San Diego, CA (US); Eva G Lovett, University City, MO (US); Joshua I Hardt, Belleville, IL (US); Kevin L Quick, Hazelwood, MO (US)

(73) Assignee: Washington University, St. Louis, MO (US)

( * ) Notice: Subject to any disclaimer, the term of this patent is extended or adjusted under 35 U.S.C. 154(b) by 104 days.

(21) Appl. No.: 11/424,175

(22) Filed: Jun. 14, 2006

(65) Prior Publication Data

US 2007/0106087 A1 May 10, 2007

Related U.S. Application Data

(60) Division of application No. 10/373,425, filed on Feb. 24, 2003, now Pat. No. 7,145,032, which is a continuation-in-part of application No. 10/083,283, filed on Feb. 23, 2002, now abandoned.

(51) Int. Cl.
*A61K 31/19* (2006.01)
(52) U.S. Cl. .................................................. 514/569
(58) Field of Classification Search ............... 514/569; 562/100
See application file for complete search history.

(56) References Cited

U.S. PATENT DOCUMENTS

| 5,648,523 | A | 7/1997 | Chiang |
| 5,739,376 | A | 4/1998 | Bingel |
| 6,265,443 | B1 | 7/2001 | Choi et al. |
| 6,538,153 | B1 | 3/2003 | Hirsch et al. |
| 6,777,445 | B2 | 8/2004 | Lei et al. |

FOREIGN PATENT DOCUMENTS

| WO | WO97046227 | 12/1997 |
| WO | WO03072802 | 9/2003 |
| WO | WO2004076349 | 9/2004 |

OTHER PUBLICATIONS

Ali et al., A Biologically Effective Fullerene (C60) Derivative With Superoxide Dismutase Mimetic Properties, Free Radical Biology & Medicine, 2004, pp. 1191-1202, vol. 37, No. 8, Elsevier.

(Continued)

*Primary Examiner*—Taylor Victor Oh
(74) *Attorney, Agent, or Firm*—Thompson Coburn LLP; Charles P. Romano

(57) ABSTRACT

Disclosed and claimed herein are e,e,e malonic acid/acetic acid tri-adducts of buckminsterfullerene of the general formula $C_{60}R_3$, wherein each R is independently selected from groups of the formula $=CR^1R^2$ wherein each $R^1$ and $R^2$ is independently selected from the group consisting of —H and —COOH, provided, however, that at least one of the $R^1$'s and $R^2$'s is a hydrogen. Processes for preparing and uses of the same for treating neuronal injury and for life-extension are also disclosed and claimed herein.

7 Claims, 14 Drawing Sheets

OTHER PUBLICATIONS

Bosi et al., "Fullerene Derivatives: An Attractive Tool for Biological Applications," Euro. J. of Med. Chem. 2003, 38: pp. 913-923.

Dugan et al., "Carboxyfullerenes as Neuroprotective Agents", Proc. Natl. Acad. Sci., Aug. 1997, 94: pp. 9434-9439.

Dugan et al. "Fullerene-based antioxidants and neurodegenerative disorders", Parkinsonism Relat. Disord. Jul. 2001; 7(3): pp. 243-246.

Keaney et al., "Superoxide dismutase mimetics elevate superoxide dismutase activity in vivo but do not retard aging in the nematode *Caenorhabditis elegans*", Free Radic. Biol. Med., Jul. 15, 2004; 37(2): pp. 239-250.

Bisaglia, M., et al., C3-fullero-tris-methanodicarboxylic acid protects cerebellar granule cells from apoptosis, Journal of Neurochemistry, 2000, vol. 74 No 3, pp. 1197-1204.

Yin-Ling Lin, et al., Light-independent inactivation of Dengue-2 virus by carboxyfullerene C3 isomer, Virology, 2000, vol. 275, pp. 258-262.

Monti, D., et al., C60 carboxyfullerene exerts a protective activity against stress-induced apoptosis in human peripheral blood mononuclear cells, Biochemical and Biophysical Research Comminacations, 2000, vol. 277, pp. 711-717.

Tsao, N., et al., Inhibition of group A streptococcus infection by carboxyfullerene, Antimicrobial Agents and Chemotherapy, Jun. 2001, vol. 45 No. 6 pp. 1788-1793.

Ali, et al, A Biologically Effective Fullerene (C60) Derivative With Superoxide Dismutase Mimetic Properties, Free Radical Biology & Medicine, 2004, pp. 1191-1202, vol. 37 No. 8, Elsevier.

Ben-Shlomo et al., Investigation by Parkinson's Disease Research Group of United Kingdom into Excess Mortality Seen with Combined Levodopa and Selegiline Treatment in Patients with Early, Mild Parkinson's Disease: Further Results of Randomised Trial and Confidential Inquiry, British Medical Journal, 1998, vol. 316, pp. 1191-1196.

Birkmayer, et al., Increased Life Expectancy Resulting from Addition of L-Deprenyl to Madopar.RTM. Treatment in Parkinson's Disease: A Longterm Study, Journal of Neural Transmission, 1985, vol. 64, pp. 113-127.

Carillo, et al., A High Dose of Long Term Treatment with Deprenyl Loses Its Effect on Antioxidant Enzyme Activities As Well As On Survivals of Fischer-344 Rats, Life Sciences, 2000, vol. 67, pp. 2539-2548.

Henry, et al., Report of the IDECG Working Group on the Biology of Aging, European Journal of Clinical Nutrition, 2000, S:157-159.

Holden, C., The Quest to Reverse Time's Toll, Science, 2002, vol. 295, pp. 1032-1033.

Honda, et al., Oxidative Stress and Life Span Determination in the Nematode *Caenorhabditis elegans*, Annals New York Academy of Sciences, 2002, pp. 466-474, New York Academy of Sciences.

Ingram, et al., Chronic Treatment of Ages Mice with L-Deprenyl Produces Marked Striatal MAO-B Inhibition but No Beneficial Effects on Survival, Motor Performance, or Nigral Lipofuscin Accumulation, Neurobiology of Aging, 1993, vol. 14, pp. 431-400.

Jordens, et al., Prolongation of Life in an Experimental Model of Aging in *Drosphila melanogaster*, Neurochemical Research, 1999, vol. 24 No. 2, pp. 227-233.

Kitani, et al., Chronic Treatment of (—)Deprenyl Prolongs the Life Span of Male Fischer 344 rats: Further Evidence, Life Science, 1993, vol. 52, pp. 281-288.

Knoll, The Striatal Dopamine Dependency of Life Span in Male Rats: Longevity Study with (—)Deprenyl, Mechanisms of Ageing and Development, 1988, vol. 46, pp. 237-262.

Larsen, P., Aging and resistance to oxidative damage in *Caenorhabditis elegans*, Procedure National Academy Science USA, Oct. 1993, vol. 90, pp. 8905-8909, Genetics.

Lee, et al., Gene Expression Profile of Aging and Its Retardation by Caloric Restriction, Science, Aug. 27, 1999, vol. 285, pp. 1390-1393.

National Institute on Aging, National Institutes of Health, Interventions Testing Program [retrieved on Jul. 18, 2005]. Retrieved from the Internet: <URL: http://www.nia.nih.gov/ResearchInformation/ScienceResources/InterventionsTestingProgram.htm.

PCT International Search Report dated Aug. 12, 2004.

Quick, et al., Rapid Microplate Assay for Superoxide Scavenging Efficiency, Journal of Neuroscience Methods, 2000, pp. 139-144.

Roth, et al., Caloric Restriction in Primates and Relevance to Humans, Annals of New York Academy Sciences, 2001, vol. 928, pp. 305-315.

Sohal, et al., Oxidative Stress, Caloric Restriction and Aging, Science, Jul 5, 1996, vol. 273, pp. 59-63.

Turturro, et al., Growth Curves and Survival Characteristics of the Animals Used in the Biomarkers of Aging Program, Journal of Gerontology: Biological Sciences, 1999, vol. 54A No. 11, pp. B492-B501, The Gerontological Society of America.

Wang, et al., Statistical Methods For Testing Effects On "Maximum Lifespan", Mechanisms of Ageing and Development, 2004, pp. 629-632, Elsevier.

Krusic et al., "Radical Reactions of C60", Science, Nov. 22, 1991: pp. 1183-1185.

Melov et al., "Extension of Life-Span with Superoxide Dismutase/Catalase Mimetics", Science, Sept. 1, 2000, pp. 1567-1569, vol. 289.

Quick and Dugan, Superoxide stress identifies neurons at risk in a model of ataxia-telangiectasia; Ann. Neurol., May 2001; 49(5): pp. 627-635.

Bis isomers
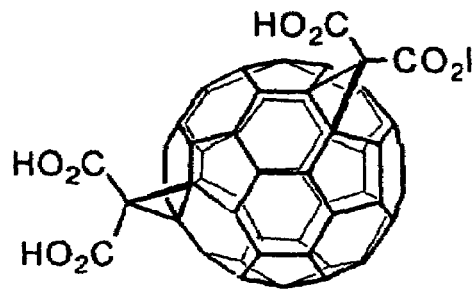
*pre-$C_3$*
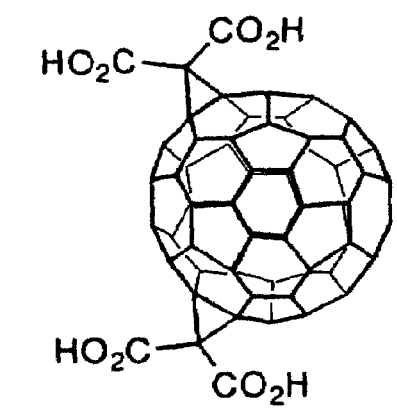
*pre-$D_3$*
Tris isomers
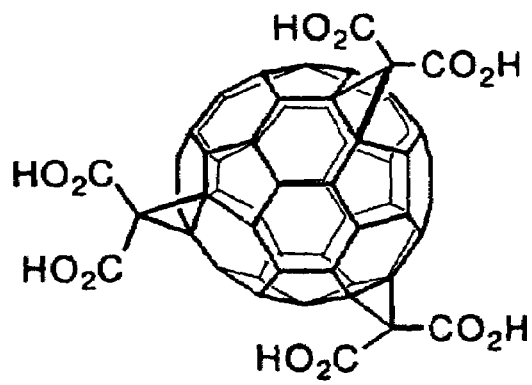
$C_3$
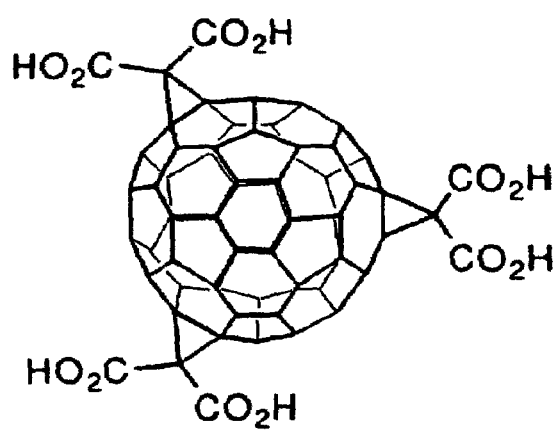
$D_3$
Tetra isomers
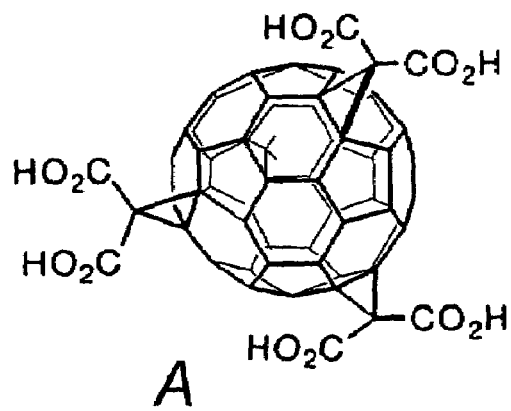
$A$
Figure 2

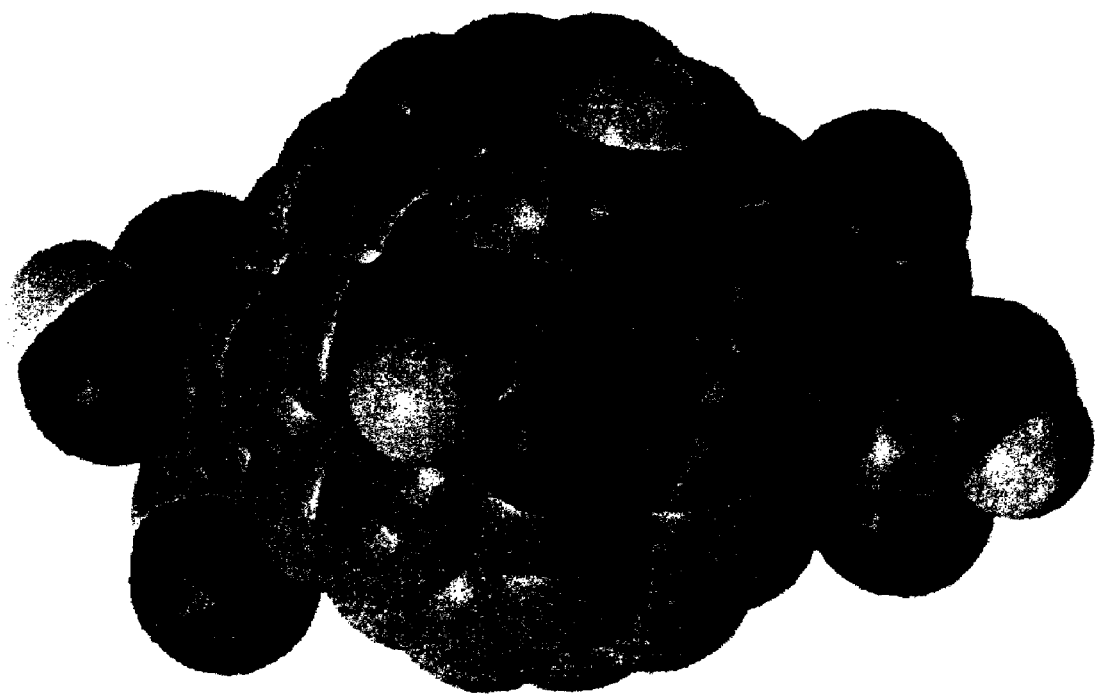
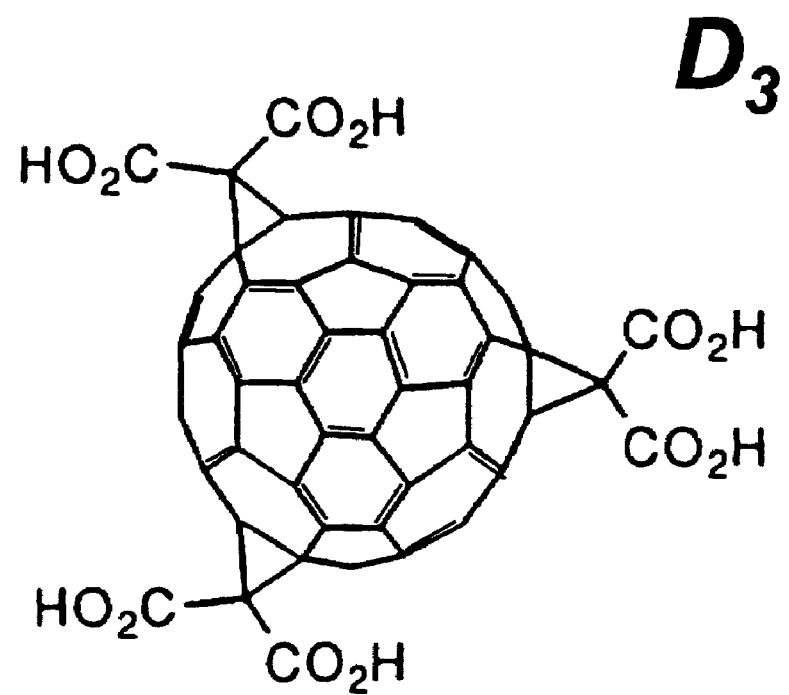
Figure 3

Group attached to cyclopropane carbon

H = Proton
Y = Internal COOH
X = External COOH
*colors indicate groups exposed to
    similar vs. different environments

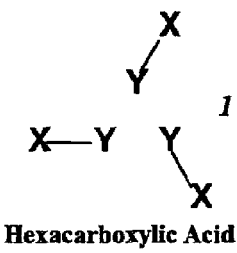

Hexacarboxylic Acid

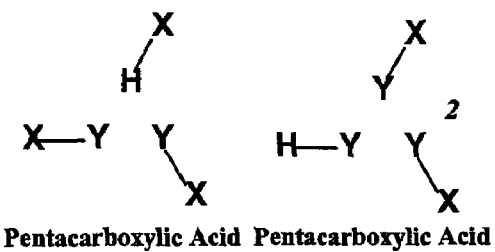

Pentacarboxylic Acid   Pentacarboxylic Acid

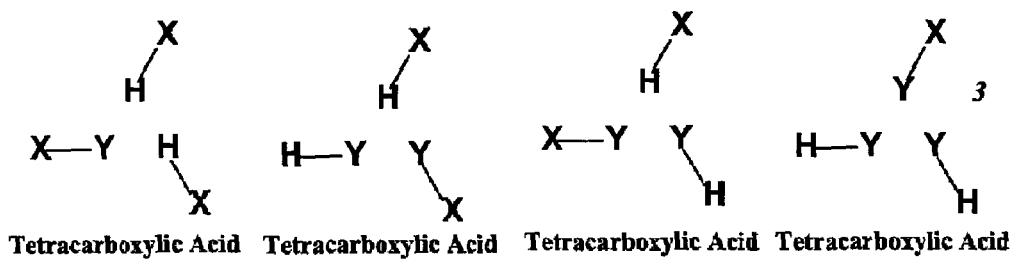

Tetracarboxylic Acid   Tetracarboxylic Acid   Tetracarboxylic Acid   Tetracarboxylic Acid

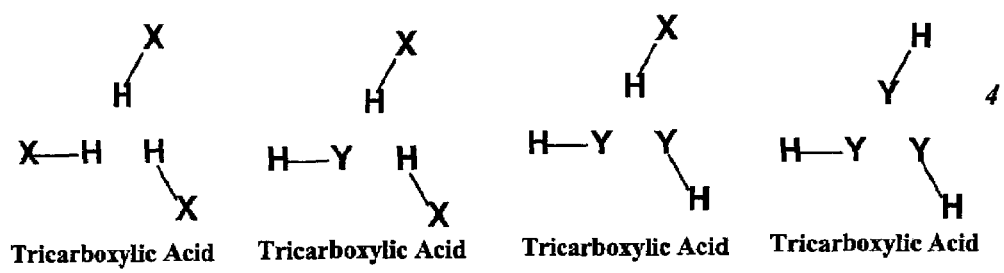

Tricarboxylic Acid   Tricarboxylic Acid   Tricarboxylic Acid   Tricarboxylic Acid

Figure 5

Configuration of functional groups on acetic acid/malonic acid $C_{60}$ derivatives.

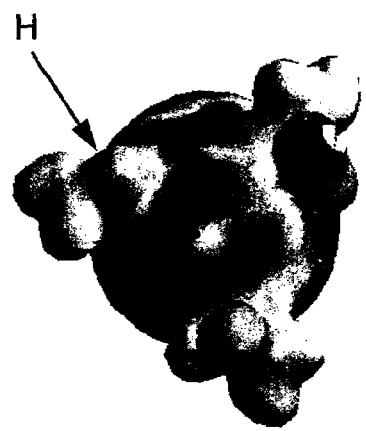
HOMO-LUMO mapping
Penta 1
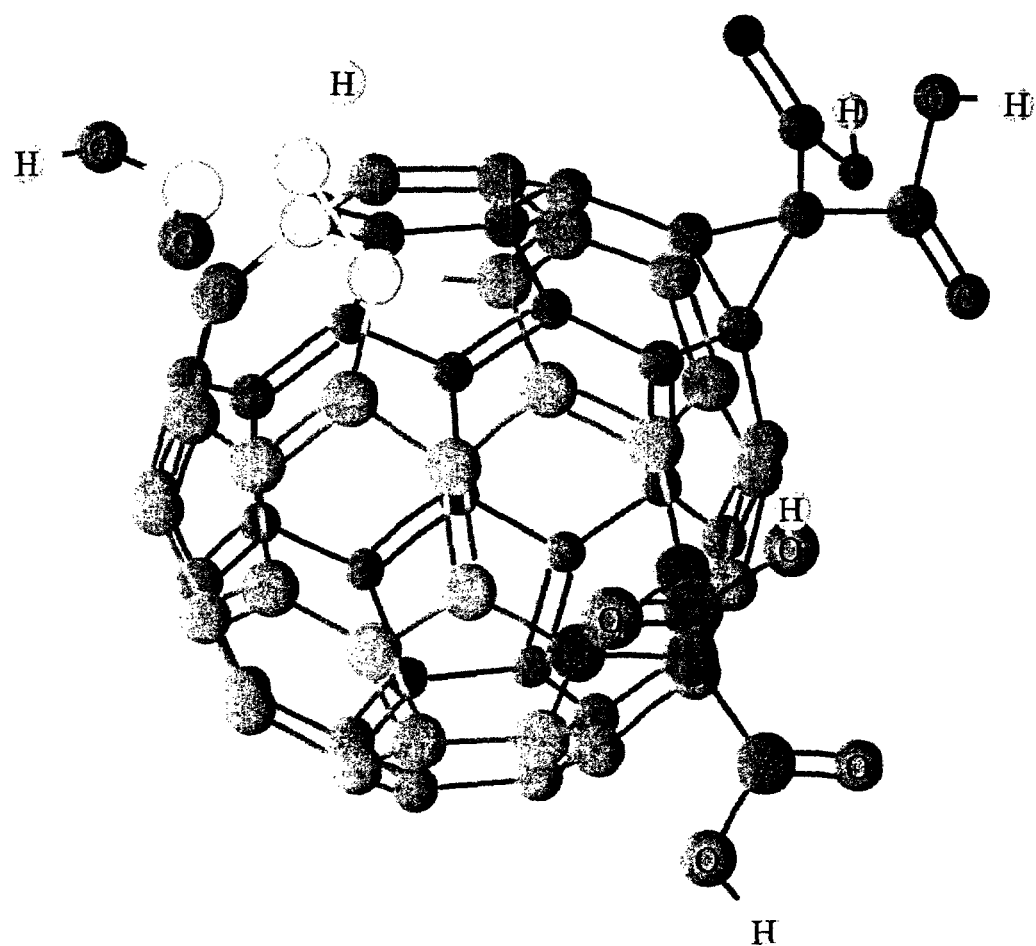
Figure 7

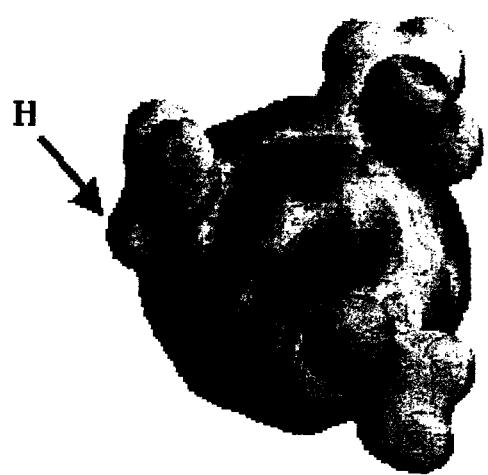
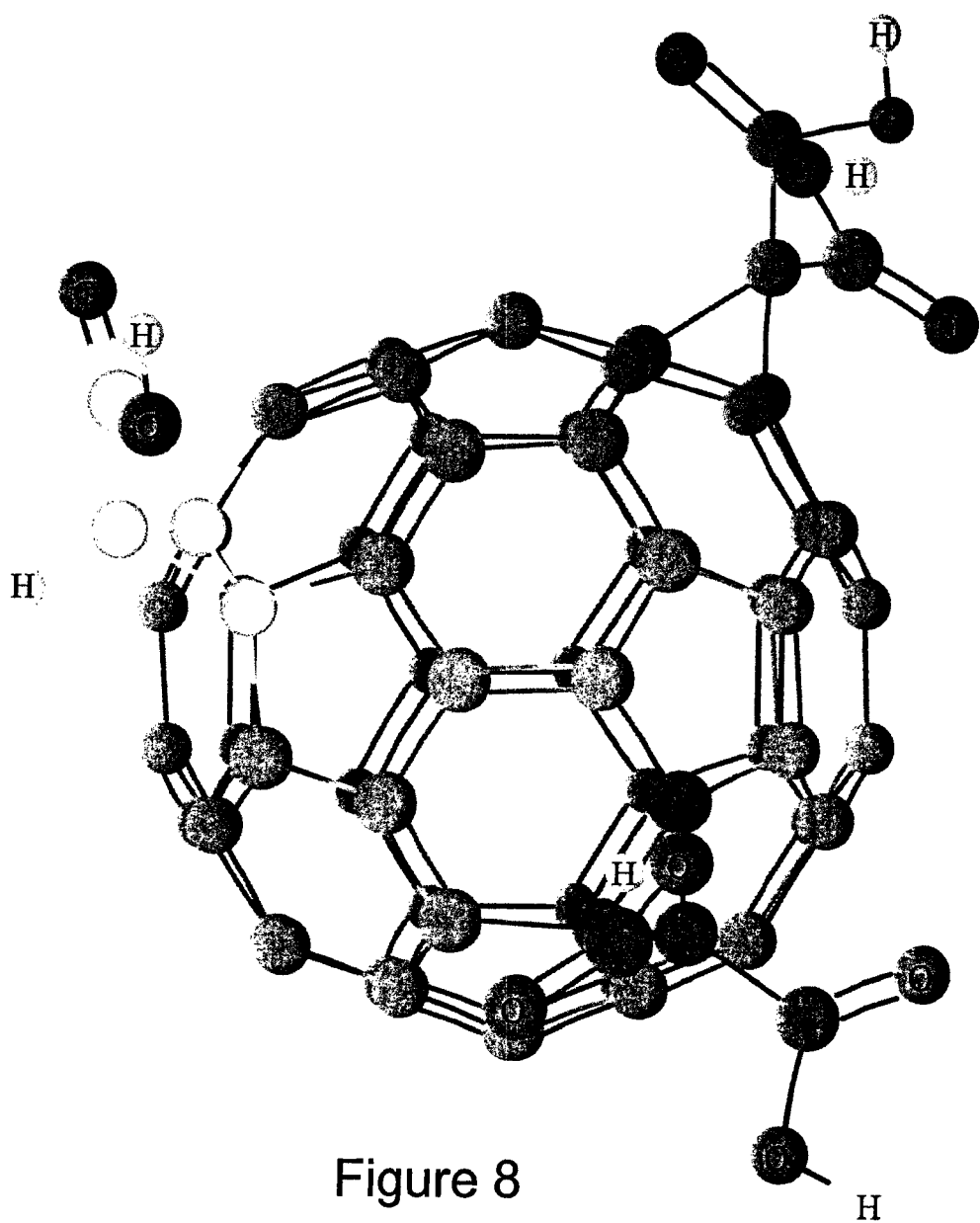
Penta 2
Figure 8

Neuroprotection by Hexa, Penta-1, Penta-2, and of $C_3$-lite versus NMDA toxicity.

Neuroprotection by Hexa, Penta-1, Penta-2, and $C_3$-lite versus AMPA toxicity.

Plasma kinetics of hexa, penta-1, and penta-2.

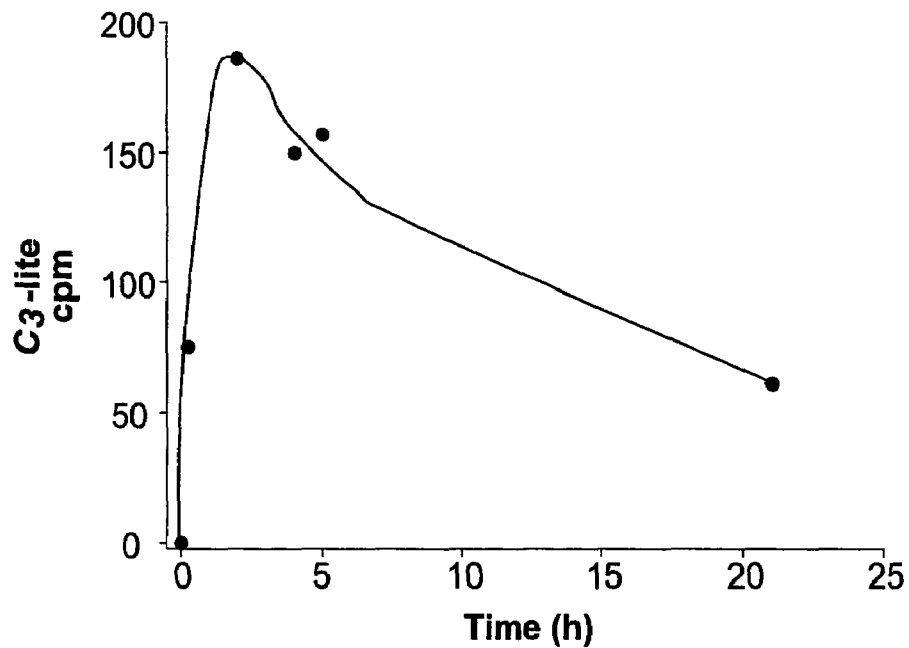
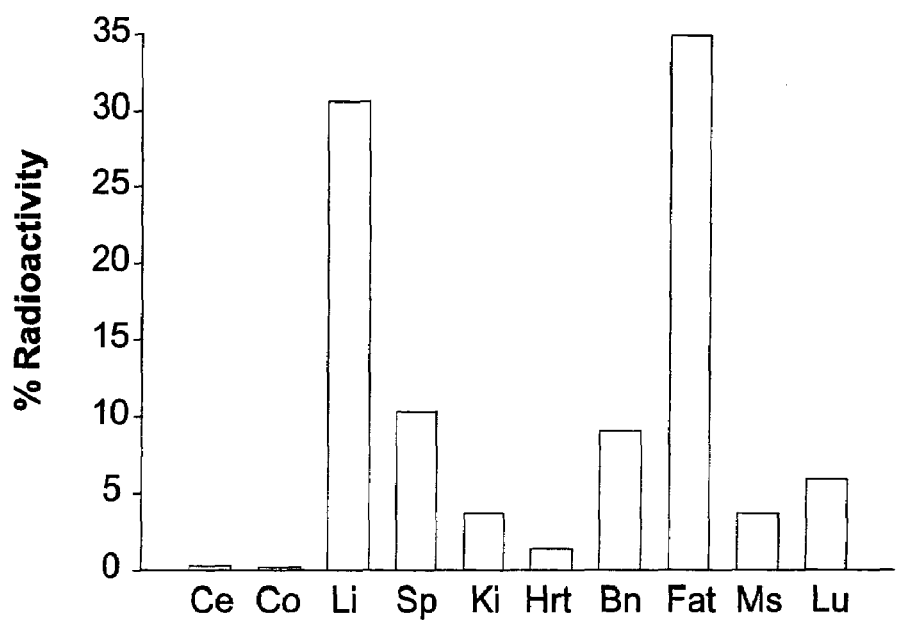
Figure 12
Plasma pharmacokinetics of $C_3$-lite.

THERAPEUTIC MALONIC ACID/ACETIC ACID $C_{60}$ TRI-ADDUCTS OF BUCKMINSTERFULLERENE AND METHODS RELATED THERETO

CROSS REFERENCE TO RELATED APPLICATIONS

This application is a divisional application of U.S. patent application Ser. No. 10/373,425, filed Feb. 24, 2003, now U.S. Pat. No. 7,145,032 which is a continuation-in-part of application Ser. No. 10/083,283; filed Feb. 23, 2002, now abandoned. U.S. patent application Ser. Nos. 10/373,425 and 10/083,283 are each incorporated herein by reference in their entireties.

STATEMENT REGARDING FEDERALLY SPONSORED RESEARCH OR DEVELOPMENT

Not applicable.

BACKGROUND OF THE INVENTION

1. Field of the Invention

The present invention relates to novel $C_{60}$ derivatives, processes for preparing such derivatives and methods of treatment. In more detail, disclosed and claimed herein are (a) novel e,e,e malonic acid/acetic acid tri-adducts of buckminsterfullerene and processes for preparing the same, (b) compositions and methods of treating neuronal injury with a therapeutically effective amount of e,e,e malonic acid/acetic acid tri-adducts of buckminsterfullerene and (c) compositions and methods for prolonging the length or duration of an expected lifespan (referred to alternately as "longevity") of metazoans or in metazoan cells with a therapeutically effective amount of e,e,e malonic acid/acetic acid tri-adducts of buckminsterfullerene.

2. Related Art

Methods of enhancing the overall health and longevity of humans and their companion animals has been a very active area of research. Current thinking in the field suggests that calorie restriction may help to extend the lifespan of metazoans.

Given the conserved nature of cellular or developmental processes across metazoans, a number of model organisms have been employed to study longevity, including *C. elegans* and *D. melanogaster*.

For example, the genetic analysis of *C.elegans* has revealed several genes involved in lifespan determination. Mutations in Daf-2 (the insulin receptor) and Clk-1 ("Clock 1", a gene affecting many aspects of developmental and behavioral timing) have been shown to extend the lifespan of adults. However, Clk-1 mutants have a higher mortality rate in early life. At later stages of development, the Clk-1 mutants show an increase in longevity, perhaps by selecting for long-lived individuals in early life. The Clk-1 longevity phenotype is abolished by mutations in the gene encoding catalase, which is involved in superoxide/free radical metabolism. Additionally, elimination of coenzyme Q in *C. elegans* diet has been shown to extend lifespan.

*C. elegans* harboring mutations in the Eat gene have also shown an increased longevity, but exhibit decreased food intake and slowed metabolism. The enhanced longevity associated with this mutation has been attributed to calorie restriction, which has been shown to also increase longevity in metazoans.

In *Drosophila*, superoxide dismutase (SOD) and catalase over expression increased the lifespan of fruit flies by 35%. Mutations also in the Methuselah gene ("Mth") have been shown to increase lifespan by 20%. The function of Mth, a G-protein coupled receptor, is not known, but mutants have shown an increased resistance to paraquat (a superoxide radical injury inducing agent) toxicity, suggesting it may be a stress-response gene.

Calorie restriction (CR) has been shown to increase lifespan by 25-35% in all animals studied to date (mice, rats, several species of monkeys, dogs, humans, as well as non-metazoan species such as spiders, Nematodes, and *Drosophila*). (NB: All animals are metazoans.) However, caloric intake needs to be reduced by as much as 30-40% to achieve robust effects on longevity. Ongoing studies in rhesus and squirrel monkeys at the National Institute of Aging ("NIA") (Roth et al., Eur. J. Clin. Nutr. S: 157, 2000) found biochemical changes in calorie restricted monkeys similar to changes reported in rodents thereby supporting the universal nature of calorie restriction on biochemical processes across vertebrate species.

Recently, 2-deoxyglucose has been used to produce calorie restriction without limiting oral intake. Animals treated with 2-deoxyglucose have lowered body temperature and decreased plasma insulin levels, similar to changes observed in calorie-restricted animals (Roth et al., Ann. N Y Acad. Sci., 928: 305, 2001). While scientific studies on the effect of 2-deoxyglucose on longevity have not been completed, a recent editorial in Science (Feb. 8, 2002) quoted the principal investigator of these studies (George Roth, NIA) as saying that one of his monkeys treated with 2-deoxyglucose lived 38 months instead of the mean survival of 25 months. However, such a claim is not scientifically supported given the small sample size. No comment was made on the age of the longest-lived monkeys in the control populations.

Increases of up to 20% in the expected lifespan of mice has been shown through growth factor deprivation, either through genetic manipulation or the administration of growth factor antagonists. Unfortunately, dwarfism is a side effect of growth factor deprivation. In humans, dwarfism, or late-life growth hormone deficiency, appears to reduce longevity, further confusing the issue of whether growth factor deprivation is effective as a means for increasing the duration of the expected lifespan.

Several papers have indicated that deprenyl (a selective monoamine oxidase (MAO) B inhibitor used to treat Parkinson's disease) increases the lifespan of many species. (See, e.g. Knoll, Mech Ageing Dev. 46:237, 1988). In one study, chronic treatment of rats with deprenyl from age 96 weeks through the end of life "enhanced survival". Control rats lived 147+/−1 weeks, whereas the deprenyl-treated rats lived 198+/−2 weeks. However, the expected mean lifespan for these rats, clearly stated in the paper, was 182 weeks, so the control group in this study appears to have had early mortality. Other studies from these laboratories selected for high-performing rats, which were then enrolled in the deprenyl longevity studies, thereby potentially artificially skewing the results.

A second study used Fisher 344 rats (Kitani et al., Life Sci 52:281, 1993), initiating deprenyl treatment at 18 months of age. The mean survival of the controls was 28 months, and of the treated animals was 30 months, showing an increase in longevity of 7%. However, these results were shown to be not statistically significant.

In contrast, another study in Fisher 344 rats with the same dose of deprenyl (Carillo et al., Life Sci 67:2539, 2000), observed greater mortality and shortened lifespan in the deprenyl-treated animals. Furthermore, a study from the NIA failed to show any survival benefit in C57B6 mice given chronic deprenyl treatment starting at 18 months of age (Ingram et al., Neurobiol Aging 14:431, 1993). Likewise, a controlled study of deprenyl in *Drosophila* did not show an increase in lifespan (Jordens et al., Neurochem Res 24:227, 1999).

Human trials of deprenyl likewise show conflicting results regarding longevity. An "open, uncontrolled" trial of deprenyl in Parkinson's patients showed an increase survival at 9 years (Birkmayer et al., J Neural Transm. 64:113, 1985), although other studies have suggested increased mortality in PD patients taking deprenyl, especially in conjunction with L-dopa (e.g. Ben-Shlomo et al., BMJ 316:1191, 1998).

Overall, the data suggest that deprenyl may or may not have weak effects on longevity.

Several genes in mice have been identified as "longevity" genes because mice with mutations in these genes have greater mean lifespans relative to the expected lifespan of control mice. These genes include the Ames dwarf mutation, and the Snell dwarf mutation. However, these mutations result in small, frail mice which have difficulty feeding. It is believed that the longevity conferred by these mutations is essentially due to calorie restriction. Recent attempts to use gene array analysis, or other genetic screens for genes associated with longevity phenotypes in worms, flies, and rodents have come up with a number of candidate genes. In general, however, they are frequently "stress-response" genes.

Many compounds, such as Gingko, Ginseng, Vitamin C, have been proposed to improve survival, but controlled and statistically significant survival studies reporting the benefit for these compounds are unknown. Vitamin C and a number of drugs reduce the incidence of certain disease conditions, e.g., cardiovascular disease, and so, presumably, would enhance overall longevity.

Buckminsterfullerene, $C_{60}$, is a carbon sphere with 12 pentagons and 20 hexagons, soluble in aromatic solvents but not in water.

Use of $C_{60}(C(COOH)_2)_n$, wherein n is an integer from 1 to 4, is disclosed for treating neuronal injury in U.S. Pat. No. 6,265,443, issued Jul. 24, 2001 to Choi et al., incorporated herein by reference in its entirety.

The preparation of $C_3$ hexacarboxylic ("$C_3$" or "Hexa") acid reported in the literature produces mixtures of products, some unidentified, with poor reproducibility and variable performance on cell culture screening.

SUMMARY OF THE INVENTION

It is in view of the above that the compositions and processes described and claimed below were developed.

A first embodiment comprises the administration of a composition to metazoans with the result of increasing the metazoan's lifespan, said composition comprising a carboxylated derivative of a $C_{60}$ fullerene ("carboxyfullerene"), such as a $C_{60}$ compound having x pairs of adjacent carbon atoms bonded to a pendant carbon wherein said pendant carbon atom is further bonded to two groups of the general formula —COOH and —R, wherein R is independently selected from the group consisting of —COOH and —H, and wherein x is at least 1.

Another embodiment of a useful compound can be described by the general formula $C_{60}$ [(CHCOOH)]$_x$[C(COOH)$_2$]$_y$, wherein x is an integer from 0 to 3, y is an integer from 1 to 4 and x plus y is an integer from 2 to 4.

An additional embodiment is e,e,e malonic acid/acetic acid tri-adducts of buckminsterfullerene of the general formula $C_{60}R_3$, wherein each R is independently selected from groups of the formula =CR1R2 wherein each $R^1$ and $R^2$ is independently selected from the group consisting of —H and —COOH, provided, however, that at least one of the $R^1$'s and $R^2$'s is a hydrogen. More particular embodiments comprise the Penta Pair, Tetra Quartet and $C_3$-lite malonic acid/acetic acid tri-adducts of buckminsterfullerene (described in more detail below).

An additional embodiment comprises an e,e,e tri-adduct of buckminsterfullerene of the general formula $C_{60}R_3$, wherein each R is independently selected from groups of the formula =$CR^1R^2$ wherein each R1 and R2 is independently selected from the group consisting of —H, —COOH and —COOMe, provided, however, that at least one of the $R^1$'s and $R^2$'s is a hydrogen or a —COOMe.

A further embodiment comprises processes of preparing e,e,e malonic acid/acetic acid tri-adducts of buckminsterfullerene of the general formula =$CR^1R^2$, wherein each R is independently selected from groups of the formula —$CR^1R^2$ wherein each $R^1$ and $R^2$ is independently selected from the group consisting of —H and —COOH, provided, however, that at least one of the $R^1$'s and $R^2$'s is a hydrogen, including the Penta Pair, Tetra Quartet and $C_3$-lite e,e,e malonic acid/acetic acid tri-adducts of buckminsterfullerene.

Yet, additional embodiments comprise the use of novel e,e,e malonic acid/acetic acid tri-adducts of buckminsterfullerene for treating neuronal injury and for life-extension (similar to $C_3$).

It is believed the use of carboxyfullerenes, including e,e,e malonic acid/acetic acid tri-adducts of buckminsterfullerene, provides a substantial improvement over calorie restriction as a method which substantially increases the lifespan of metazoans, especially humans, given the inherent difficulties within calorie restriction (including, but not limited to, severe limits to food intake as well as the impracticability of use with humans in general). It is also shown that the novel e,e,e malonic acid/acetic acid tri-adducts of buckminsterfullerene have similar desirable properties to the $C_3$ tris malonic acid $C_{60}$ compound, but have longer half-lives in animals, thereby extending their effective period in vivo. Additionally, because e,e,e malonic acid/acetic acid tri-adducts of buckminsterfullerene, including Penta-1, Penta-2, the Tetra Quartet and $C_3$-lite, are more lipophilic than $C_3$, they can concentrate in lipid-rich tissues, such as brain.

BRIEF DESCRIPTION OF THE DRAWINGS

The accompanying drawings, which are incorporated in and form a part of the specification, illustrate various embodiments of the present invention and together with the description, serve to explain the principles of the invention. In the drawings:

FIG. 2 displays various useful carboxyfullerenes.

FIG. 3 displays the $C_3$ tris malonic acid regioisomer.

FIG. 5 details the configuration of functional groups on e,e,e malonic acid/acetic acid tri-adducts of buckminsterfullerene.

FIG. 7 depicts the structure of Penta-1.

FIG. 8 depicts the structure of Penta-2.

FIG. 12 details the plasma pharmacokinetics and tissue distribution of $C_3$-lite.

DETAILED DESCRIPTION OF THE DRAWINGS

Figure 1A:
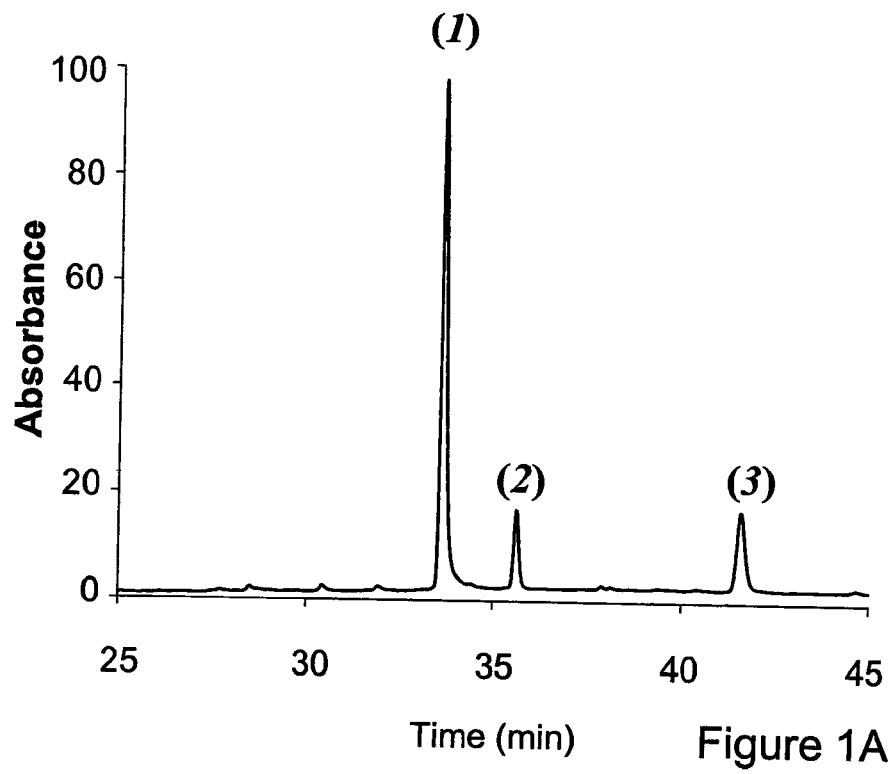
FIG. 1 discloses an analysis of $C_3$ preparations by HPLC identifying three major carboxyfullerene components.

Referring to the accompanying drawings in which like reference numbers indicate like elements:

FIG. 1a discloses an analysis of $C_3$ preparations by HPLC identifying three major components (>99% of the total).

Figure 1B:
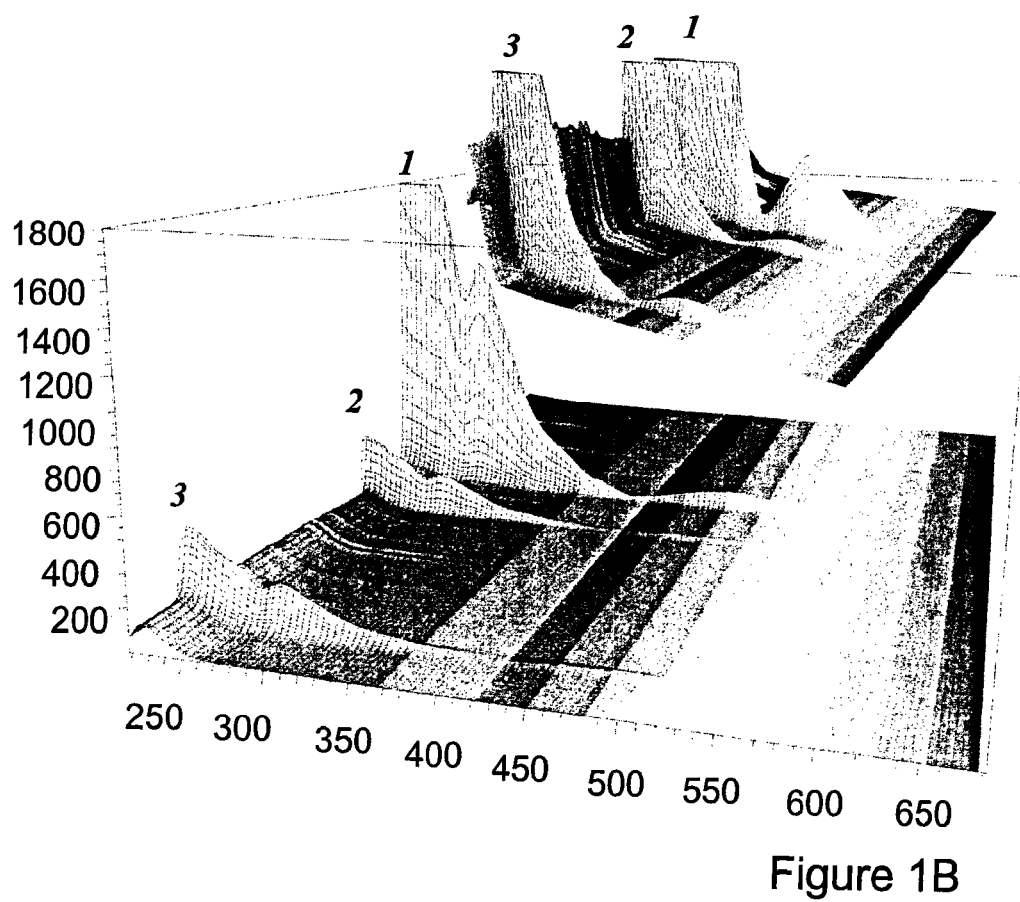

FIGS. 1b, c indicate all three of the peaks had absorbance spectra characteristic of e,e,e ($C_3$) additions to the $C_{60}$ nucleus indicating that the component peaks of $C_3$ represented e,e,e regioisomers with different headgroups attached to the cyclopropane carbons on $C_{60}$.

Figure 1C:
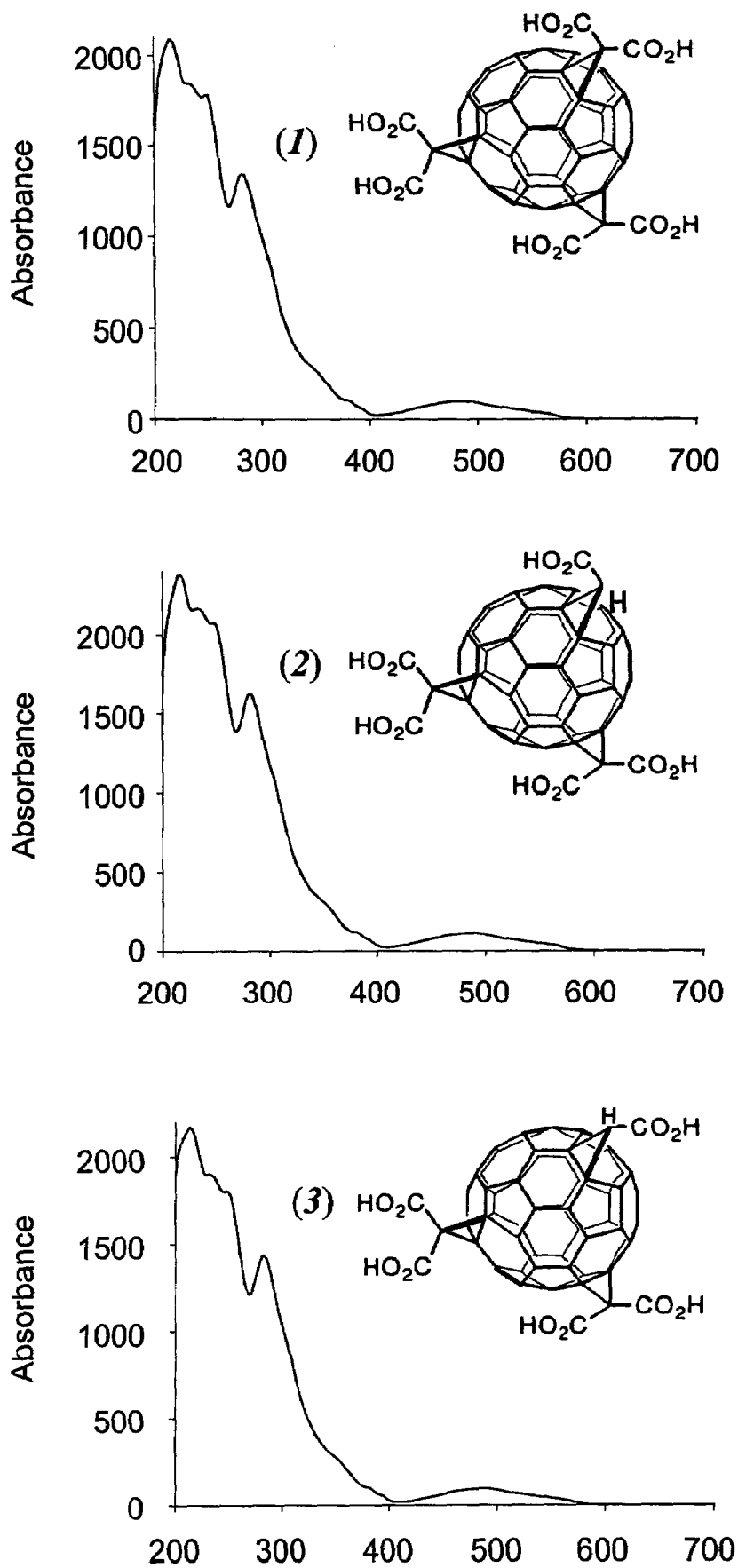

FIGS. 1c(1)-1c(3) show compounds 1-3, separated by HPLC, and then determined by mass spectrometry to be Hexacarboxylic acid $C_3$ (1, 80%) and two isomeric Pentacarboxylic acids (2 and 3, 10% each).

Figure 1D:
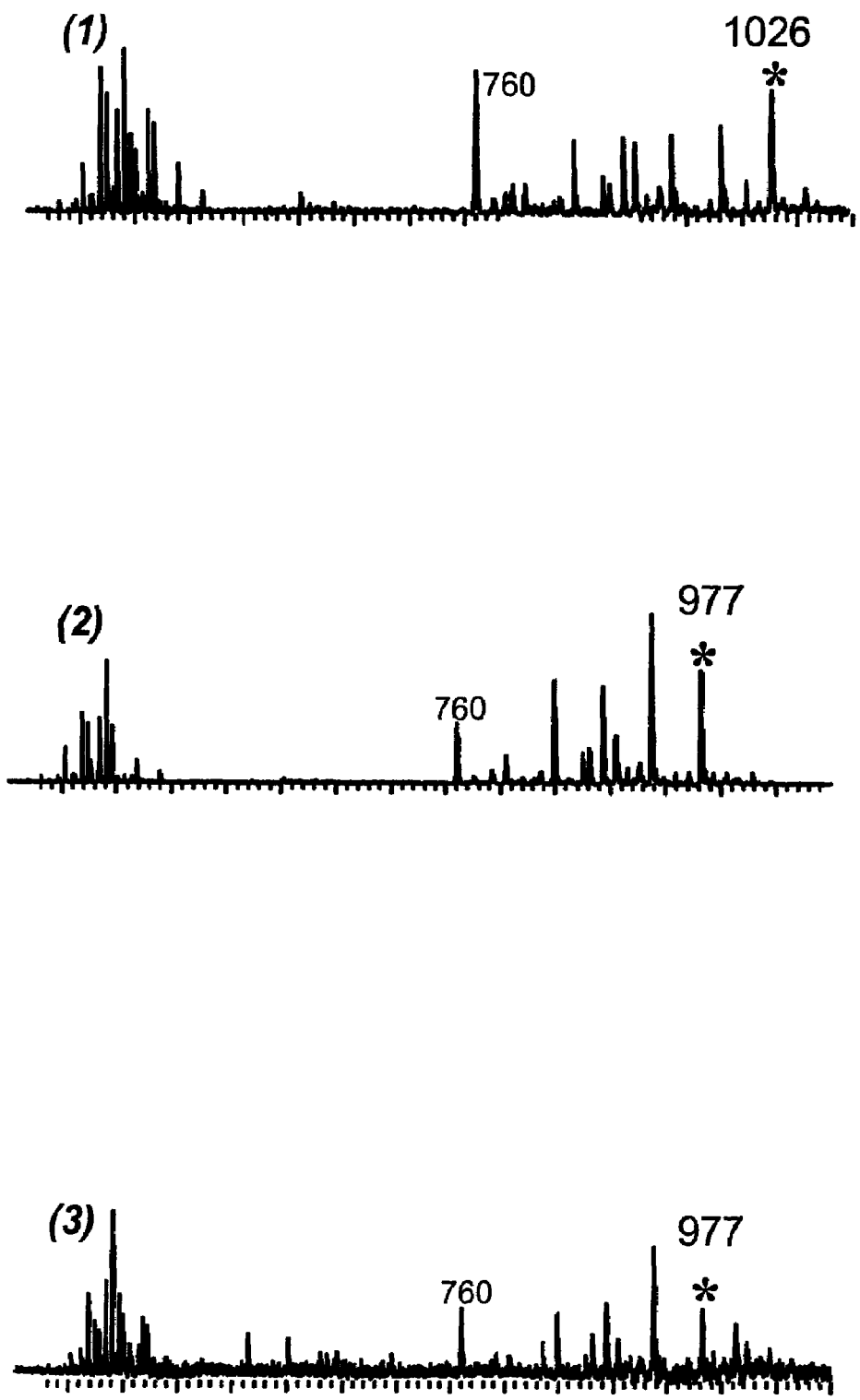

FIGS. 1d(1)-1d(3) shows mass spectroscopy performed on the Hexa isomer (1), and each Pentacarboxylic acid (2), (3).

FIG. 2 depicts various carboxyfullerenes, including 2 bis isomers, 2 tris isomers and a tetra isomer.

FIG. 3 depicts the e,e,e tris malonic acid regioisomer with $C_3$ symmetry ("$C_3$") as both a space filling structure and a chemical structure.

Figure 4:
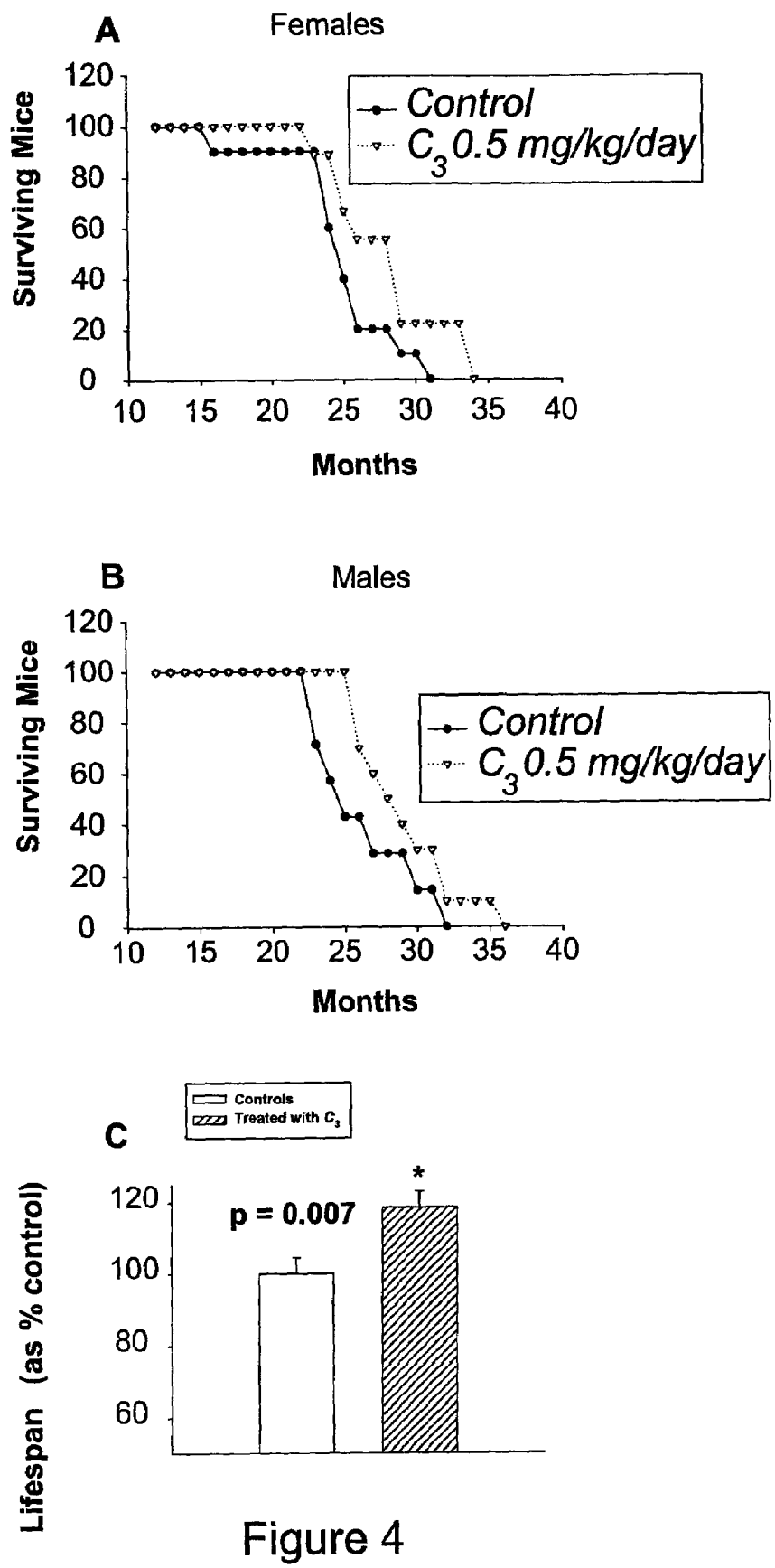
FIG. 4 depicts the survival of C57B6 mice treated with oral $C_3$ vs. control solution.

FIG. 4 is a Kaplan-Meier survival curve showing lifespan of C57B6 mice treated with either food coloring (control) or $C_3$ (0.5 mg/kg/day) in their drinking water from the age of 12 months through the end of life. The date of spontaneous death for each mouse was recorded, and used to calculate the lifespan. Lifespan of each mouse was calculated in months because mice received from the NIA rodent colony have their birth month, but not their specific birth date, recorded. Average survival was calculated for each treatment and the mean lifespans were compared using a t-test with significance set to p<0.05 (actual p=0.033). Data from the first cohort is graphed by gender (A, B) and combined (C), with each treatment group compared to same-sex controls. Weights (g) in treated and untreated mice (by gender) were not different, e.g., at 19 mos, weights for females: ctrl 27±1, $C_3$-treated 29±1; for males: ctrl 35±4, $C_3$-treated 35±6, Mean±SD.

FIG. 5 details the configuration of functional groups on e,e,e malonic acid/acetic acid tri-adducts of buckminsterfullerene.

Figure 6:
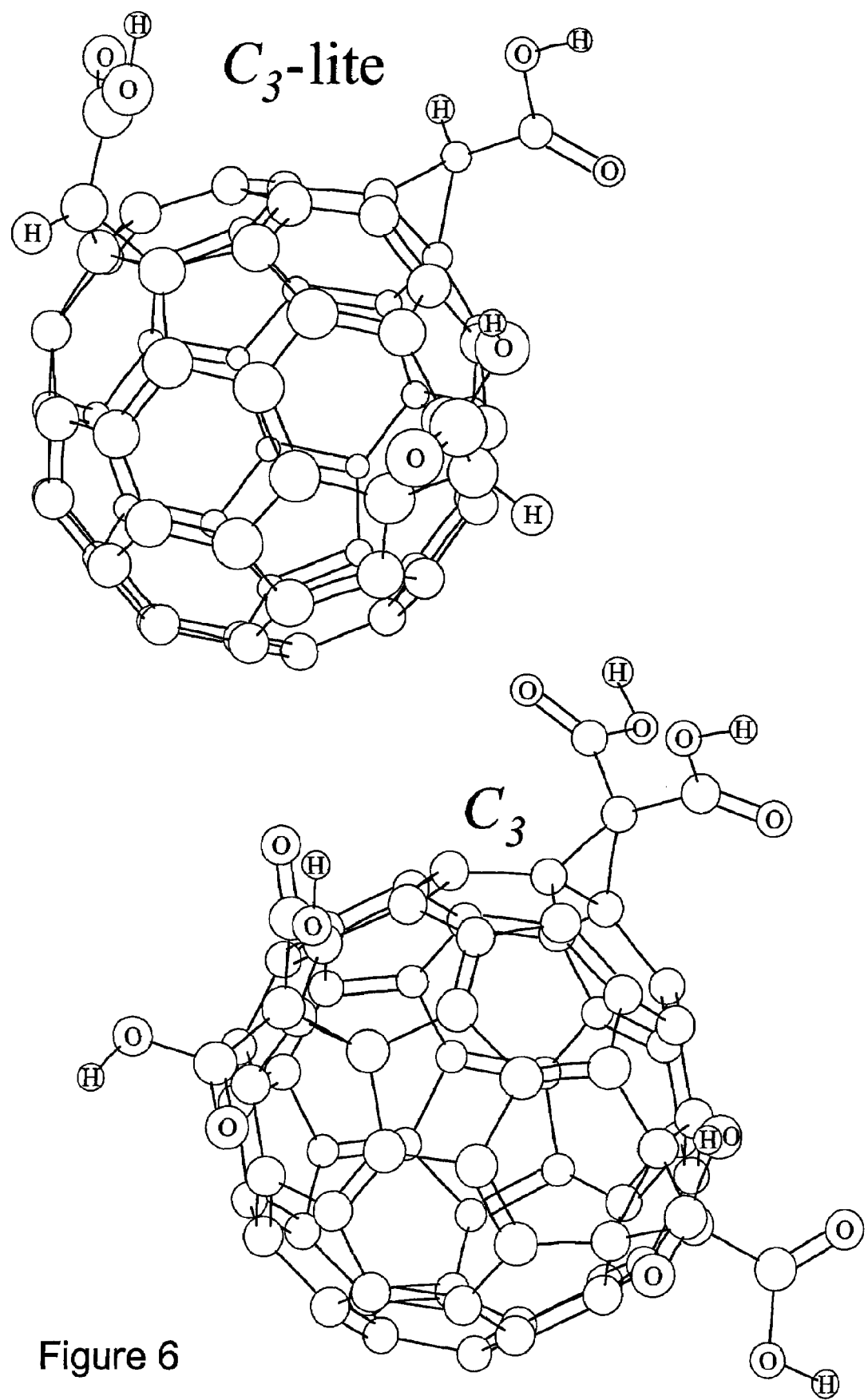
FIG. 6 depicts structures of $C_3$-lite (e,e,e tris acetic acid $C_{60}$) and $C_3$ (e,e,e tris malonic acid $C_{60}$).

FIG. 6 depicts structures of $C_3$-lite (e,e,e tris acetic acid $C_{60}$) and $C_3$. $C_3$-lite differs from $C_3$ in that one of the pair of carboxylic acids attached to each of the three cyclopropane carbons is replaced with a proton.

FIG. 7 depicts the structure of the Penta-1 compound. HOMO-LUMO energy distribution (top), and ball and stick (bottom). For Penta-1, one of the malonic acid groups of $C_3$ has been replaced by an acetic acid group. In Penta-1, the proton faces in towards the two malonic acid groups FIG. 8 depicts the structure of the Penta-2 compound. HOMO-LUMO energy distribution (top), and ball and stick (bottom). For Penta-2, one of the malonic acid groups of $C_3$ has been replaced by an acetic acid group. In Penta-1, the proton faces away from the two malonic acid groups.

Figure 9:
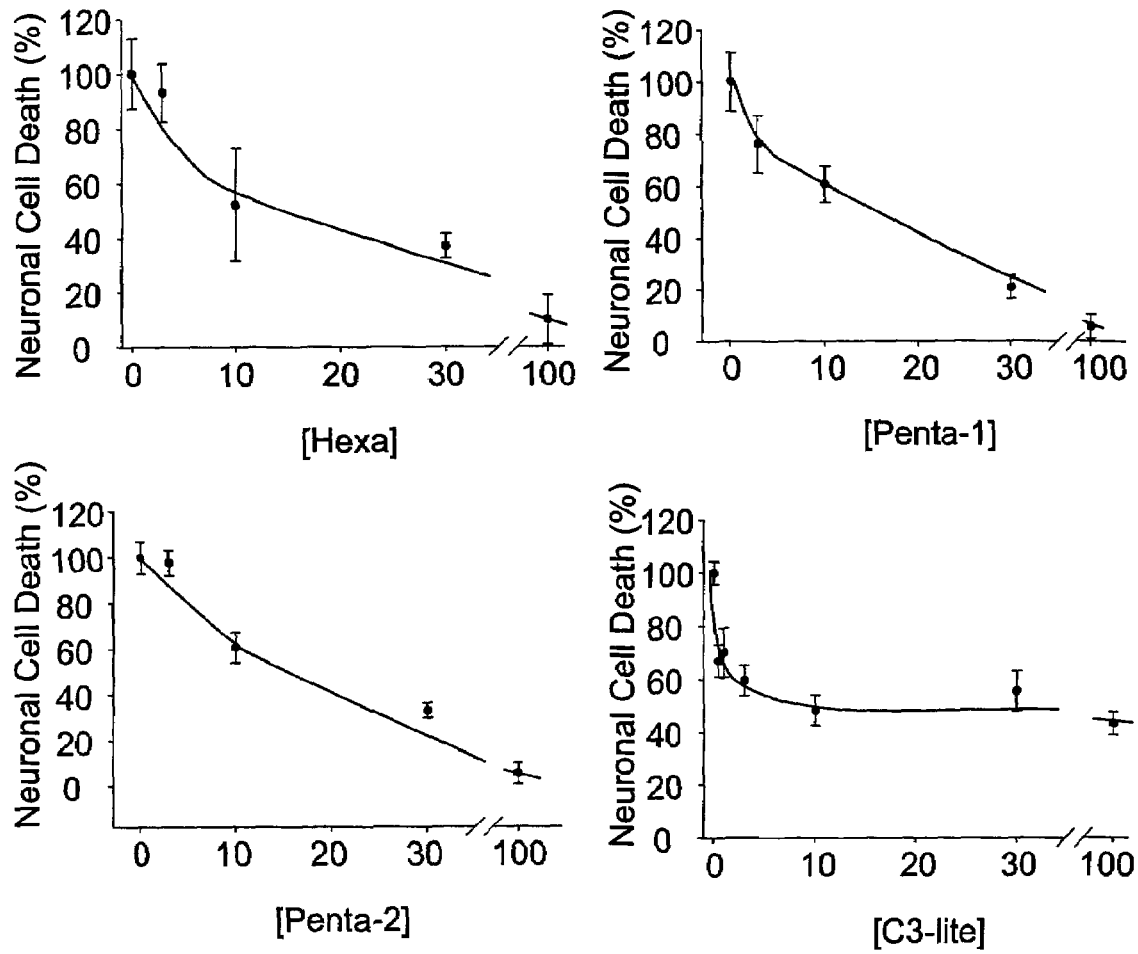
FIG. 9 depicts neuroprotection by Hexa, Penta-1, Penta-2, and $C_3$-lite versus NMDA toxicity.

FIG. 9 depicts neuroprotection by the e,e,e malonic acid/acetic acid tri-adducts of buckminsterfullerene Hexa, Penta-1, Penta-2, and $C_3$-lite in cerebrocortical cell cultures versus NMDA receptor-mediated excitotoxicity. Cultures were exposed to 200 µM NMDA for 10 minutes, with or without $C_3$ derivatives (0.5-100 µM). All drugs were washed out after 10 minutes, and cells were returned to the cell culture incubator for 24 hours. Neuronal cell death was then assessed by measuring release of lactate dehydrogenase (LDH) by dying neurons. Cell death and protection was confirmed by imaging propidium iodide staining of dead neurons and by evaluating neuronal morphology using phase contrast microscopy. Dose response curves for each compound are shown. Values represent the % cell death observed in cultures exposed to NMDA alone (with no $C_{60}$ derivative).

Figure 10:
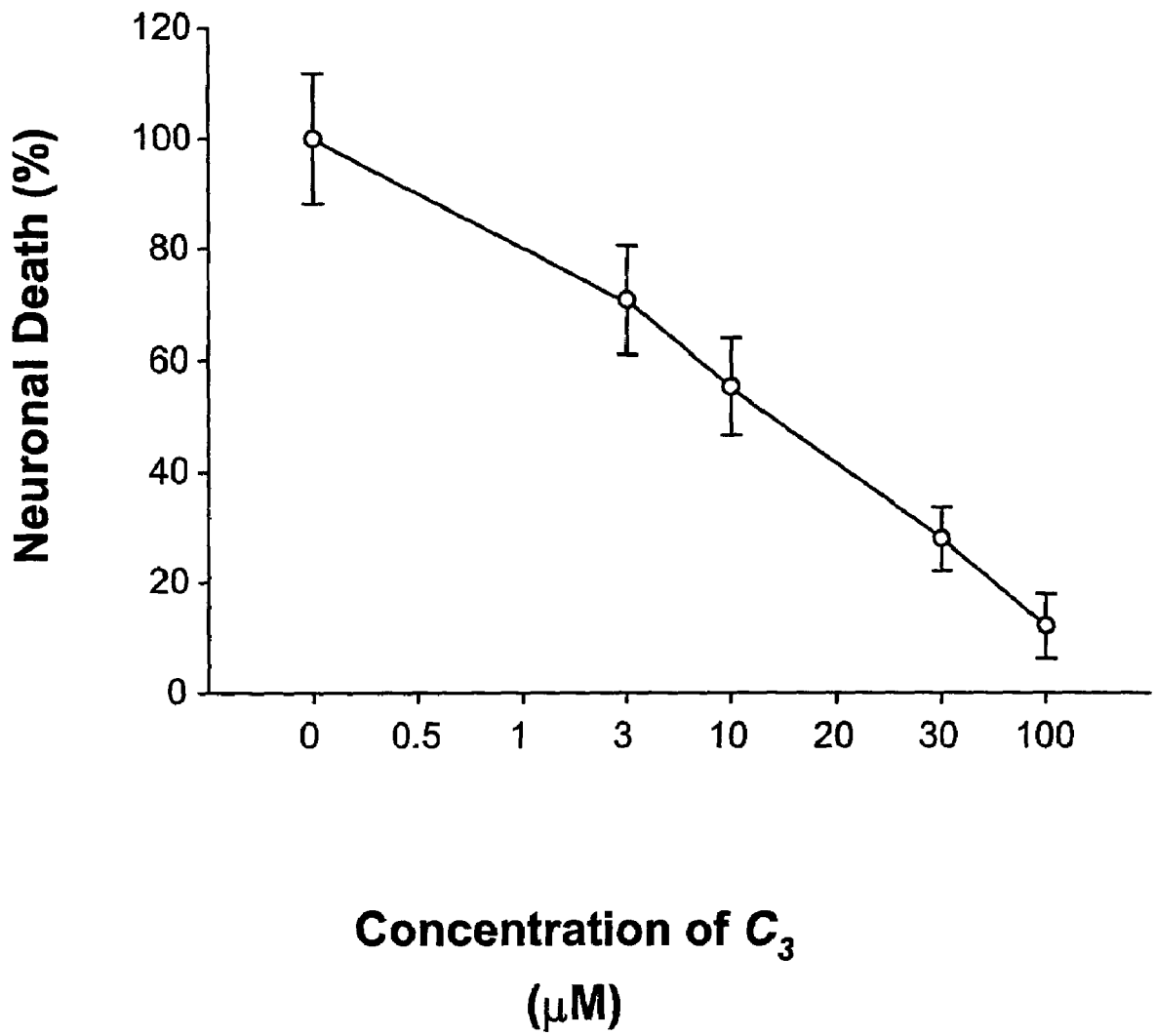
FIG. 10 depicts neuroprotection by Hexa, Penta-1, Penta-2, and $C_3$-lite versus AMPA toxicity.

FIG. 10 depicts neuroprotection by the e,e,e malonic acid/acetic acid tri-adducts of buckminsterfullerene Hexa, Penta-1, Penta-2, and $C_3$-lite in cerebrocortical cell cultures versus AMPA receptor-mediated excitotoxicity. Cultures were exposed to 6 µM AMPA for 24 hours, with or without $C_3$ derivatives (0.5-100 µM). Neuronal cell death was assessed at 24 hours by measuring release of lactate dehydrogenase (LDH) by dying neurons. Cell death and protection was confirmed by imaging propidium iodide staining of dead neurons and by evaluating neuronal morphology using phase contrast microscopy. Dose response curves for each compound are shown. Values represent the % cell death observed in cultures exposed to AMPA alone (with no $C_{60}$ derivative).

Figure 11:
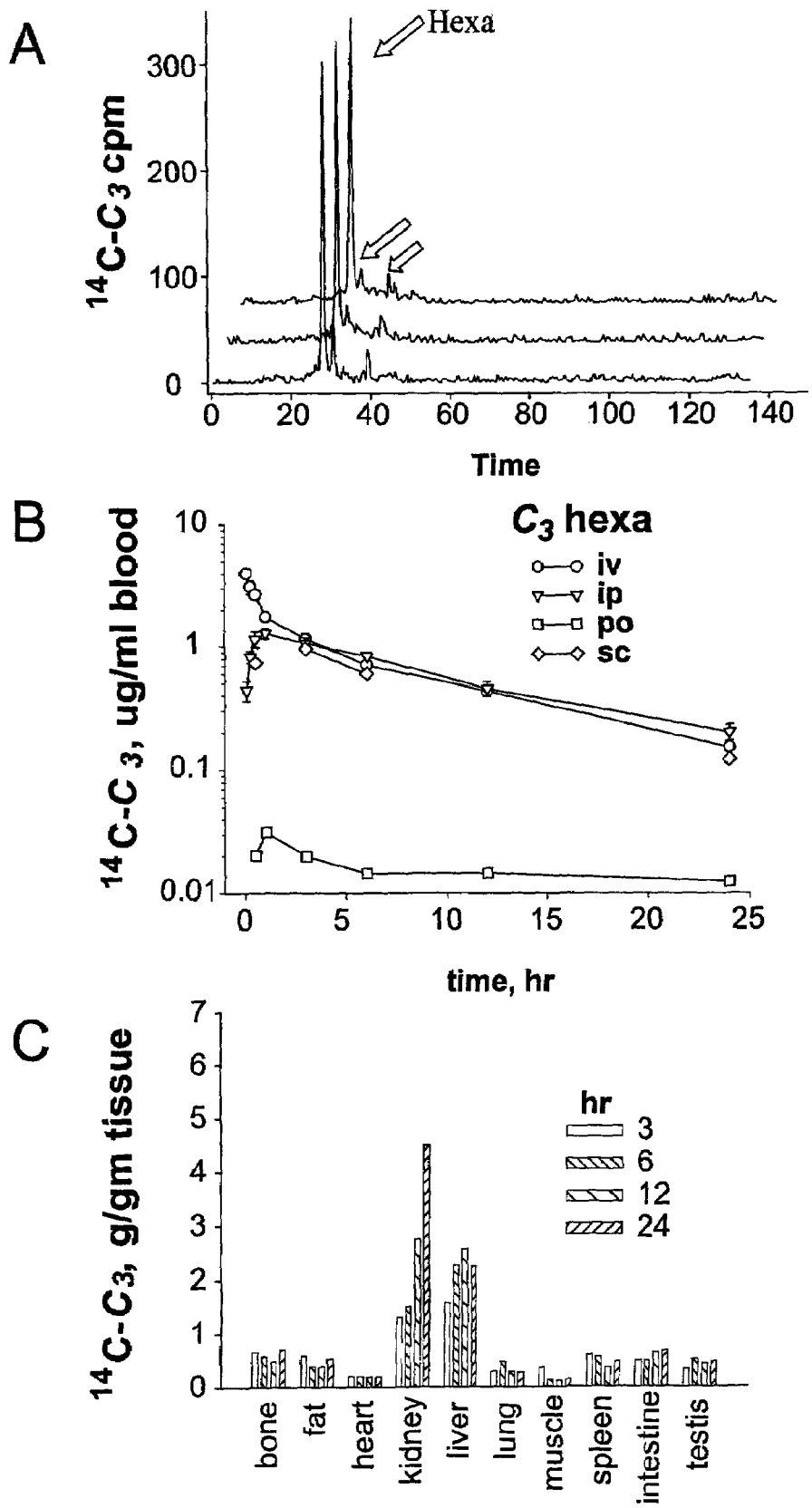
FIG. 11 details the plasma kinetics of Hexa, Penta-1 and Penta-2, and the tissue distribution of $C_3$.

FIG. 11 depicts the plasma pharmacokinetics of Hexa, Penta-1, and Penta-2, (A-B) and tissue distribution of Hexa $C_3$ (C). FIG. 11 (A) is an HPLC analysis of plasma from mice injected with $^{14}C$—$C_3$ containing 80% Hexa, 10% Penta-1, 10% Penta-2. Samples were t=0 ($C_3$ sample before injection), t=2 hours (plasma 2 hours after i.p. injection of $C_3$), t=18 hours (plasma 18 hours after injection). FIG. 11 (B) depicts plasma levels after iv, ip, sc and po administration of $C_3$. The plasma $T_{1/2}$ for Hexa, Penta-1 and Penta-2 were all 8.2 hours. FIG. 11 (C) depicts tissue levels of $C_3$ at various times after ip administration showing accumulation through the liver and kidney.

FIG. 12 depicts plasma pharmacokinetics and tissue distribution of $C_3$-lite. FIG. (A) shows the plasma pharmacokinetics of $^{14}C$—$C_3$-lite and demonstrates a $T_{1/2}$ of 15 h. FIG. 12 (B) depicts the tissue distribution of $C_3$-lite after ip administration.

DETAILED DESCRIPTION OF THE INVENTION

The following terminology will be utilized throughout:

"Lifespan" or "expected lifespan," is the average expected length of life (from birth to death) that a metazoan would be expected to live (i.e., "generic" expected lifespan) in a particular environment if that metazoan were not treated with carboxyfullerenes.

"Malonic acid/acetic acid $C_{60}$ derivatives" are acetic acid derivatives of $C_{60}$, malonic acid derivatives of $C_{60}$ and mixed malonic acid/acetic acid derivatives of $C_{60}$.

"Hexa" and $C_3$ represent $C_3(C_{60}(C(COOH)_2)_3$, where the malonic acid groups are all at the e,e,e positions (compound 1, below).

"Pentas" or "Penta Pair" means $(C_{60}(C(COOH)_2)_2(C(CHCOOH))$, where the R-groups are attached to cyclopropane carbons at the e,e,e positions. There are two stereoisomers Penta-1 and Penta-2 (compound 2, below).

"Tetras" or "Tetra Quartet" means $(C_{60}(C(COOH)_2)(C(CHCOOH))_2$, wherein acetic acid/malonic acid groups are attached to cyclopropane carbons at the e,e,e positions. There are four stereoisomers (compound 3, below).

"$C_3$-lite" means $(C_{60}(CHCOOH))_3$ wherein the acetic acid groups are attached to cyclopropane carbons at in the e,e,e positions. There are four stereoisomers (compound 4, below).

"An e,e,e malonic acid/acetic acid tri-adduct of buckminsterfullerene" or "malonic acid/acetic acid $C_{60}$ derivative" means a buckminsterfullerene with three pendant groups independently selected from malonic groups (>C(COOH)$_2$) and acetic groups (>CHCOOH) at the e,e,e positions; to wit:

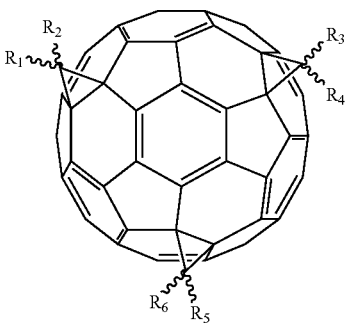

| Compound | R-Groups |
|---|---|
| 1 | $R_1 = R_2 = R_3 = R_4 = R_5 = R_6 = $ COOH ($C_3$) |
| 2 | $R_1 = $ H, $R_2 = R_3 = R_4 = R_5 = R_6 = $ COOH (Penta Pair) |
| 3 | $R_1 = R_3 = $ H, $R_2 = R_4 = R_5 = R_6 = $ COOH (Tetra Quartet) |
| 4 | $R_1 = R_3 = R_5 = $ H, $R_2 = R_4 = R_6 = $ COOH ($C_3$-lite) |
| 5 | $R_1 = R_2 = $ COOt-Bu, $R_3 = R_4 = R_5 = R_6 = $ COOMe |
| 6 | $R_1 = R_2 = R_3 = R_4 = $ COOt-Bu, $R_5 = R_6 = $ COOMe |
| 7 | $R_1 = R_2 = $ COOH, $R_3 = R_4 = R_5 = R_6 = $ COOMe |
| 8 | $R_1 = R_2 = R_3 = R_4 = $ COOH, $R_5 = R_6 = $ COOMe |
| 9 | $R_1 = $ H, $R_2 = $ COOH, $R_3 = R_4 = R_5 = R_6 = $ COOMe |
| 10 | $R_1 = R_3 = $ H, $R_2 = R_4 = $ COOH, $R_5 = R_6 = $ COOMe |

Carboxyfullerenes, Including e,e,e Malonic Acid/Acetic Acid Tri-adducts of Buckminsterfullerene, for Prolonging the Expected Length or Duration of a Lifespan Many important biological reactions generate reactive oxygen species intentionally, or as unwanted toxic by-products. While reactive oxygen species, including superoxide ($O_2^-$) and hydrogen peroxide ($H_2O_2$), are harnessed for specific physiological functions, they also pose an ongoing threat to the viability and integrity of cells and tissues. In response, cells and organisms have developed a variety of mechanisms to defend themselves against $O_2^-$ and $H_2O_2$. In metazoans, $O_2^-$ is removed by two metallo-enzymes, Cu, Zn-superoxide dismutase (SOD1), and MnSOD (SOD2). $H_2O_2$, in turn, is removed by catalase, a heme iron containing metallo-enzyme, or glutathione peroxidase, a family of proteins which utilize selenocysteines in conjunction with glutathione to convert $H_2O_2$ to $O_2$ and $H_2O$. However, these endogenous antioxidant defense systems may be overwhelmed under pathological conditions. This has led to attempts to develop additional antioxidants (useful substances that inhibit oxidation or inhibit reactions promoted by oxygen or peroxides) as small molecules to supplement the antioxidant defenses of cells as potential therapeutic agents.

A number of water-soluble $C_{60}$ derivatives (superoxide dismutase-mimetics) retain the antioxidant properties of their parent fullerene molecule, allowing its free radical scavenging abilities to be exploited in biological systems and thereby act as agents which reduce cell damage and death.

One group of $C_{60}$ derivatives, carboxyfullerenes, act as a decomposition catalyst for $H_2O_2$ and $O_2^-$. Although, manganese-containing protoporphyrin compounds, including MnT-MPyp, have been reported to act as decomposition catalysts for $O_2^-/H_2O_2$, these compounds rely on oxidation-reduction of the manganese atom to catalyze decomposition. It has been now discovered by the inventors that although $C_3$ is a non-metallic compound, it too possesses similar catalytic properties. It is believed this compound is the first non-metallic compound to act in such a manner.

Because many important biological reactions generate reactive oxygen species intentionally, or as unwanted toxic by-products, antioxidant molecules capable of supplementing the antioxidant defenses of cells as potential therapeutic agents are therapeutically useful. This includes carboxyfullerenes such as e,e,e malonic acid/acetic acid tri-adducts of buckminsterfullerene. These novel carboxyfullerene compositions have antioxidant properties. Through our research, the reactivity of $C_3$ with $O_2^-$ and $H_2O_2$ was characterized. The $K_i$ of $C_3$ for $O_2^-$ was calculated to be $3 \times 10^6$ M$^{-1}$ sec$^{-1}$. Analysis of $C_3$ after interaction with $O_2^-$ and $H_2O_2$ indicated that no permanent chemical or structural changes occurred at either the $C_{60}$ moiety or the malonic acid groups, supporting the claim that $C_3$ is a true catalyst. Although, manganese-containing protoporphyrin and salen compounds have also been reported to act as catalysts for the decomposition of $O_2^-/H_2O_2$, these compounds rely on oxidation-reduction of the metal atom to catalyze decomposition, whereas the malonic acid fullerene derivatives do not require a metal atom to catalyze the decomposition of reactive oxygen species.

Thus, in view of the foregoing discovery, carboxyfullerenes, including e,e,e malonic acid/acetic acid tri-adducts of buckininsterfullerene are useful in the elimination of reactive oxygen species, especially reactive oxygen species that are physiologically relevant, such as hydrogen peroxide ($H_2O_2$) and superoxide ($O_2^-$).

Described and claimed herein are methods of increasing a metazoan's expected lifespan by administering therapeutically effective amounts of antioxidants which result in an extended metazoan, or metazoan's cell, lifespan. In particular, compositions comprising the antioxidant carboxyfullerenes are used as treatments to increase the lifespan of metazoans or metazoan cells.

The compounds useful herein are thus carboxyfullerene compounds, their corresponding salts and esters having x pairs of adjacent carbon atoms of the $C_{60}$ fullerene bonded to at least one pendant carbon, wherein the pendant carbon atom is further bonded to two groups of the general formula —COOH and —R, wherein R is independently selected from the group consisting of —COOH and —H, and wherein x is at least 1. Examples of isomers of this general formula are shown in FIGS. 1-3. Also useful herein are e,e,e malonic acid/acetic acid tri-adducts of buckminsterfullerene of the general formula $C_{60}R_3$, wherein each R is independently selected from groups of the formula =CR$^1$R$^2$ wherein each R$^1$ and R$^2$ is independently selected from the group consisting of —H and —COOH, provided, however, that at least one of the R$^1$'s and R$^2$'s is a hydrogen.

Thus, provided is a method of extending the expected lifespan of metazoans or metazoan cells, including mammals and more particularly, humans, by administering to the metazoan an e,e,e malonic acid/acetic acid tri-adduct of buckminsterfullerene of the general formula $C_{60}R_3$, wherein each R is independently selected from groups of the formula =CR$^1$R$^2$ wherein each R$^1$ and R$^2$ is independently selected from the group consisting of —H and —COOH, provided, however, that at least one of the R$^1$'s and R$^2$'s is a hydrogen.

All carboxyfullerene compounds, including the e,e,e malonic acid/acetic acid tri-adducts of buckminsterfullerene, can be administered systematically as a composition containing the active compound and a pharmaceutically acceptable carrier compatible with said compound. In preparing such a composition, any conventional pharmaceutically acceptable carrier may be utilized. When the drug is administered orally, it is generally administered at regular intervals.

In therapeutic use, e,e,e malonic acid/acetic acid tri-adducts of buckminsterfullerene may be administered by any route whereby drugs are conventionally administered. Such routes include intravenous, intramuscular, subcutaneous, intrathecal, intraperitoneal, topical, and oral.

Pharmaceutical compositions comprising the e,e,e malonic acid/acetic acid tri-adducts of buckminsterfullerene of this invention can be made up in any conventional form, including a solid form for oral administration such as tablets, capsules, pills, powders, granules, and the like. These pharmaceutical compositions may be sterilized and/or may contain adjuvants such as preservatives, stabilizers, wetting agents, emulsifiers, salts for varying the osmotic pressure, and/or buffers.

Typical preparations for intravenous administration would be sterile aqueous solutions including water/buffered solutions. Intravenous vehicles include fluid, nutrient and electrolyte replenishers. Preservatives and other additives may also be present such as antibiotics and antioxidants.

The e,e,e malonic acid/acetic acid tri-adducts of buckminsterfullerene described and claimed herein are useful in pharmaceutically acceptable oral modes. These pharmaceutical compositions contain said compound in association with a compatible pharmaceutically acceptable carrier material. Any conventional carrier material can be utilized. Any conventional oral dosage form such as tablets, capsules, pills, powders, granules, and the like may be used. The carrier material can be an organic or inorganic inert carrier material suitable for oral administration. Suitable carriers include water, gelatin, gum arabic, lactose, starch, magnesium stearate, talc, vegetable oils, polyalkylene-glycols, petroleum jelly and the like. Furthermore, the pharmaceutical composition may contain other pharmaceutically active agents. Additional additives such as flavoring agents, preservatives, stabilizers, emulsifying agents, buffers and the like may be added in accordance with accepted practices of pharmaceutical compounding.

An oral dosage form may comprise, for example, tablets, capsules of hard or soft gelatin, methylcellulose or of another suitable material easily dissolved in the digestive tract. The oral dosages contemplated will vary in accordance with the needs of the individual patient as determined by the prescribing physician. An example of this oral dosage form embodiment comprises capsules or tablets containing from 50 to 500 mg of e,e,e malonic acid/acetic acid tri-adducts of buckminsterfullerene.

Methods of treatment with e,e,e malonic acid/acetic acid tri-adducts of buckminsterfullerene of this invention can generally be given to adults daily, preferably orally, intramuscularly, subcutaneously or intravenously. If intramuscularly, intravenously or subcutaneously, treatments should be given in an amount from as low as about 0.1 mg/kg to an amount as high as 3 mg/kg, with the precise dosage being varied depending upon the needs of the patient. The daily dose, if given orally, would be expected to be as little as 0.1 mg/kg to an amount as high as 15 mg/kg. In general, this therapy may be carried out prophylactically for an indefinite time.

The e,e,e malonic acid/acetic acid tri-adducts of buckminsterfullerene of the present invention may be administered chronically (e.g., daily) or frequently (e.g., once a week). The $C_3$ Hexa isomer, the Penta Pair, the Tetra Quartet and $C_3$-lite are expected to be the more effective agents. The expected daily dose of the $C_3$ isomer, if given by intravenous, intramuscular or subcutaneous delivery, would be about 0.1 mg/kg to about 3 mg/kg. The daily does if given orally would be expected to range between 0.1 mg/kg and 15 mg/kg.

The above dosing information is based on a pharmokinetics study carried out in mice, toxicity testing in mice and toxicity testing in rats. In mice, the plasma half-lives of $C_3$, Penta-1 and Penta-2 were calculated to be about 8 hours, while the plasma half-life of $C_3$-lite was about 15 hours. The 50% lethal dose (LD50) for a single injection of the carboxyfullerenes was >70 mg/kg. $C_3$, Penta-1 and Penta-2 were cleared from mice by excretion through both the liver and kidney while $C_3$-lite was cleared through the liver and fat. Using calculations based on this pharmacokinetic data, the therapeutic plasma levels appear to be between 0.1 and 1 µg/ml. Although equivalent amounts of carboxyfullerenes are absorbed if the compound is given by intravenous, intraperitoneal or subcutaneous administrations, only about $1/15^{th}$ of this dose is absorbed when given orally (e.g., in drinking water). However, the standard pharmaceutical formulations of carboxyfullerenes for oral delivery are expected to significantly increase the bioavailability of orally-administered carboxyfullerenes (e.g., incorporation of carboxyfullerenes into time-release tablets). Additionally, e,e,e malonic acid/acetic acid tri-adducts of buckminsterfullerene are more lipophilic than $C_3$, which allows them to concentrate in lipid-rich tissues, such as brain.

It is envisioned that these claimed processes are useful for all metazoans, including but not limited to vertebrates, and more specifically to mammals, including humans and their companion animals.

The lifespan increased by carboxyfullerenes is the expected average length of time (from birth to death) that a metazoan would be expected to live, if that metazoan were not treated with carboxyfullerenes. As the results of Example 2 and FIG. 4 indicate, mice subject to this treatment had an actual lifespan of 28.7 months, which corresponded to a lifespan that is about 20% greater than the control mouse's lifespan of 23.5 months. The lifespan of the control mouse used in this example represents the generic "expected lifespan."

Nonlimiting embodiments of compounds useful for extending the duration of life of a mammal, comprise compounds such as e,e,e malonic acid/acetic acid tri-adducts of buckminsterfullerene of the general formula $C_{60}R_3$, wherein each R is independently selected from groups of the formula =$CR^1R^2$ wherein each $R^1$ and $R^2$ is independently selected from the group consisting of —H and —COOH, provided, however, that at least one of the $R^1$'s and $R^2$'s is a hydrogen. Nonlimiting examples of e,e,e malonic acid/acetic acid tri-adducts of buckminsterfullerene include compounds selected from the group consisting of the Penta Pair, the Tetra Quartet, $C_3$-lite, their stereoisomers, mixtures thereof and the like.

A further nonlimiting embodiment is a process for extending the lifespan of a metazoan or metazoan cells comprising administering to said metazoan a composition comprising at least one e,e,e malonic acid/acetic acid tri-adduct of buckminsterfullerene of the general formula $C_{60}R_3$, wherein each R is independently selected from groups of the formula =$CR^1R^2$ wherein each $R^1$ and $R^2$ is independently selected from the group consisting of —H and —COOH, provided, however, that at least one of the $R^1$'s and $R^2$'s is a hydrogen. Nonlimiting examples of e,e,e malonic acid/acetic acid tri-adducts of buckminsterfullerene include compounds selected from the group consisting of the Penta Pair, the Tetra Quartet, $C_3$-lite, their stereoisomers, mixtures thereof and the like. It is envisioned that said composition would comprise at least one e,e,e malonic acid/acetic acid tri-adduct of buckminsterfullerene, its pharmaceutically acceptable salts and pharmaceutically accepted esters, and a pharmaceutically acceptable carrier, wherein the components are in said composition in a therapeutically effective amount. The e,e,e malonic acid/acetic acid tri-adduct of buckminsterfullerene can be administered intravenously, intramuscularly, subcutaneously or orally. This process can be used with all metazoans, including but not limited to vertebrates, mammals and humans.

Malonic Acid/Acetic Acid Tri-adducts of Buckminsterfullerene $C_{60}$ e,e,e malonic acid/acetic acid tri-adducts display additional desirable qualities including increased water solubility. Several novel $C_{60}$ e,e,e malonic acid/acetic acid tri-adducts have been synthesized and characterized, including: 1) acetic acid derivatives of $C_{60}$, and 2) e,e,e malonic acid/acetic acid tri-adducts of buckminsterfullerene. Two compounds (2), referred to as "Penta-1" (FIG. 7) and "Penta-2" (FIG. 8) are e,e,e derivatives of $C_{60}$ with two malonic acid groups, and one acetic acid group added to $C_{60}$. Penta-1 and Penta-2 differ in whether the proton attached to the cyclopropane carbon of the acetic acid group faces in toward the two malonic acid groups, or away from them. A second set of four compounds "the Tetra-Quartet" (3) has one malonic acid group, and two acetic acid groups in the e,e,e positions. A third set of compounds are the e,e, e tris acetic acid derivative of $C_{60}$ ($C_3$-lite) (4) (FIG. 6). These e,e,e malonic acid/acetic acid tri-adducts of buckminsterfullerene include Penta-1, Penta-2, the four Tetra's and the $C_3$-lite compounds, their pharmaceutically acceptable salts and esters.

A general formula for e,e,e malonic acid/acetic acid tri-adducts of buckminsterfullerene comprises $C_{60}R_3$, wherein each R is independently selected from groups of the formula $=CR^1R^2$ wherein each $R^1$ and $R^2$ is independently selected from the group consisting of —H and —COOH, provided, however, that at least one of the $R^1$'s and $R^2$'s is a hydrogen.

Neuroprotective e,e,e Malonic Acid/Acetic Acid Tri-adducts of Buckminsterfullerene Because many important biological reactions generate reactive oxygen species intentionally, or as unwanted toxic by-products, antioxidant molecules capable of supplementing the antioxidant defenses of cells as potential therapeutic agents are therapeutically useful.

The e,e,e malonic acid/acetic acid tri-adducts of buckminsterfullerene derivatives described and claimed herein may be used to prevent, treat or ameliorate the progression of any disease condition caused by free radicals, especially when the free radicals are released as a result of glutamate neurotoxicity ("excitotoxicity"). Treating excitotoxic injury means reducing the extent of damage to central neurons which have been damaged by glutamate released from surrounding cells. Neurotoxic events such as excitotoxicity can occur during many types of acute neurological insults such as hypoxia/ischemia, such as occurs during stroke, hypoglycemia, epilepsy or trauma. Neurotoxic events may also be involved in chronic neuronal damage caused by neurodegenerative disorders such as Huntington's disease, Alzheimer's disease, amyotropic lateral sclerosis ("ALS"), and the neurodegenerative effects of AIDS. Thus, e,e,e malonic acid/acetic acid tri-adducts of buckminsterfullerene also are useful in methods of treating diseases in which a neurotoxic injury occurs.

Arachidonic acid ("AA") is released in neurons due to an influx of excessive $Ca^{2+}$ into the neuronal cells which is caused by NMDA receptor stimulation by glutamate (the glutamate having been released by neurons which were damaged by the neurotoxic event, itself). The excessive $Ca^{2+}$ influx activates phospholipase $A_2$, a calcium-dependent enzyme which breaks down cell membranes liberating the AA. The metabolism of AA by endogenous lipoxygenases and cyclooxygenases leads to the production of the oxygen free radicals that trigger peroxidative degradation of neuronal lipid membranes which results in the neuronal damage or death. Therefore, reducing oxygen-derived free radicals by administering a composition comprising a free radical scavenging e,e,e malonic acid/acetic acid tri-adduct of buckminsterfullerene provides an alternative mechanism by which glutamate-induced neurotoxicity is inhibited.

Similar to the above processes and compositions for increasing the lifespan of individuals, compositions and methods for treating neurotoxic injury in a patient suffering a neurotoxic injury comprises administering to said patient a composition comprising a therapeutically effective amount of e,e,e malonic acid/acetic acid tri-adducts of buckminsterfullerene to that individual. More in particular, these embodiments comprise the administration of at least one e,e,e malonic acid/acetic acid tri-adduct of buckminsterfullerene of the general formula $C_{60}R_3$, wherein each R is independently selected from groups of the formula $=CR^1R^2$ wherein each $R^1$ and $R^2$ is independently selected from the group consisting of —H and —COOH, provided, however, that at least one of the $R^1$'s and $R^2$'s is a hydrogen. A further embodiment comprises the administration of $C_3$-lite, Penta-1, Penta-2 and the Tetra Quartet to the patient. Methods of treatment with these novel compounds can be intravenous, intramuscular, subcutaneous or through oral delivery.

A first embodiment comprises compounds for the treatment of neuronal injury. Nonlimiting examples of such compounds include e,e,e malonic acid/acetic acid tri-adducts of buckminsterfullerene of the general formula $C_{60}R_3$, wherein each R is independently selected from groups of the formula $=CR^1R^2$ wherein each $R^1$ and $R^2$ is independently selected from the group consisting of —H and —COOH, provided, however, that at least one of the $R^1$'s and $R^2$'s is a hydrogen. Additional nonlimiting examples of e,e,e malonic acid/acetic acid tri-adducts of buckminsterfullerene include compounds selected from the group consisting of the Penta Pair, the Tetra Quartet, $C_3$-lite, their stereoisomers, mixtures thereof and the like.

A second embodiment comprises a method of treating neurotoxic injury in a patient suffering a neurotoxic injury by administering to said patient a composition comprising an e,e,e malonic acid/acetic acid tri-adduct of buckminsterfullerene of the general formula $C_{60}R_3$, wherein each R is independently selected from groups of the formula $=CR^1R^2$ wherein each $R^1$ and $R^2$ is independently selected from the group consisting of —H and —COOH, provided, however, that at least one of the $R^1$'s and $R^2$'s is a hydrogen, its pharmaceutically acceptable salts and pharmaceutically acceptable esters, and a pharmaceutically acceptable carrier, wherein said compound is present in said composition in an amount effective to treat said neurotoxic injury. Nonlimiting examples of e,e,e malonic acid/acetic acid tri-adducts of buckminsterfullerene useful for the treatment of neurotoxic injury include e,e,e malonic acid/acetic acid tri-adducts of buckminsterfullerene selected from the group consisting of the Penta Pair, the Tetra Quartet, $C_3$-lite, their stereoisomers, mixtures thereof and the like.

As indicated above, the compounds of this method can be administered in amounts from about 1.5 mg/kg to about 1500 mg/kg daily or from about 10 mg/kg to about 60 mg/kg daily.

A third embodiment is a method of inhibiting neurotoxic injury in a patient where said injury is caused by free radical oxygen species released by neurons due to the stimulation by glutamate of NMDA receptors of said neurons by administering to said patient a composition comprising an e,e,e malonic acid/acetic acid tri-adduct of buckminsterfullerene of the general formula $C_{60}R_3$, wherein each R is independently selected from groups of the formula $=CR^1R^2$ wherein each $R^1$ and $R^2$ is independently selected from the group consisting of —H and —COOH, provided, however, that at least one of the $R^1$'s and $R^2$'s is a hydrogen, its pharmaceutically acceptable salts and pharmaceutically acceptable esters, and a pharmaceutically acceptable carrier, wherein said compound is present in said composition in an amount effective to inhibit said neurotoxic injury. Nonlimiting examples of e,e,e malonic acid/acetic acid tri-adducts of buckminsterfullerene useful for this process include compounds selected from the group consisting of the Penta Pair, the Tetra Quartet, $C_3$-lite, their stereoisomers, mixtures thereof and the like.

The e,e,e malonic acid/acetic acid tri-adducts of buckminsterfullerene can be administered in amounts from about 1.5 mg/kg to about 1500 mg/kg daily, or in an amount from about 10 mg/kg to about 60 mg/kg daily.

Chemical Synthesis of e,e,e Malonic Acid/Acetic Acid Tri-adducts of Buckminsterfullerene The preparation of $C_3$ reported in the literature produces mixtures of products, some unidentified, with poor reproducibility and variable performance on cell culture screening. Therefore, more reliable and direct processes to specific components are necessary.

Methods of Synthesizing High Concentrations of Hexa

Using the below methods of synthesis, large quantities of Hexa can be generated, with results generally greater than 90, 94 and 97%.

One such process involves preparing an initial solution of water, methanol and $C_3$ methyl ester in a solvent. The mole ratio of water to ester is between about 100:1 to about 20:1. Solvents useful for dissolving the $C_3$ methyl ester include aromatic solvents such as toluene, t-butyl acetate in toluene or the like. The initial solution is then mixed thoroughly (approximately 1 hour) and may appear cloudy at first. Sodium hydroxide, up to about 1 M, in methanol is next added, after which the solution is stirred vigorously until no color remains in solution (up to about 2 hours). To ensure the reaction is complete, TLC could be used.

Once the reaction is complete, water is added to form a nonaqueous layer and an aqueous layer. The layers are then separated by any standard method including but not limited to decanting, using a separatory funnel, or any other equipment useful for separating layers. Any residual solvent is then stripped in vacuo. The aqueous layer, which contains the product, is heated in an inert atmosphere ($N_2$ or the like) at about 60° C. for about 1 to about 2 hours.

The isomer distribution can be determined utilizing HPLC protocols 1 and 2 (below) and generally is above 90, 94 or 97%.

Direct Synthesis of the Penta Pair or Tetra Quartet By Decarboxylation

The Penta Pair or the Tetra Quartet are directly synthesized by initially adding an ester of bromomalonate (including, but not limited to dimethyl bromomalonate) to di-t-butylmalonyl $C_{60}$ (as prepared by Bingel, U.S. Pat. No. 5,739,376, incorporated herein by reference in its entirety) in an aromatic solvent chosen to maximize solubility, such as toluene or benzene, followed by a tertiary amine, including but not limited to 1,8-diazabicyclo (5,4,0) undec-7-ene ("DBU") or sodium hydride (prepared as disclosed in Bingel '376 at Col. 4, lines 44-45) to form a reaction mixture. To prepare the Penta Pair, these reactants are in a 1:2:2 $C_{60}$ to malonate to base ratio concentration. To prepare the Tetra Quartet, a 1:1:1 ratio is utilized. A suitable time (about 30 minutes) should be allowed to pass to ensure thorough mixing of the reaction mixture. The end point of the reaction can be determined by TLC. The reaction mixture is next poured onto a column of silica gel in the solvent selected above. To separate the bis isomers, the column should be eluted with the solvent until all of the bis isomers come off. The solvent should then be changed to ethyl acetate/solvent mixtures and should be added in increasing concentrations of ethyl acetate, such as 0.5% to 1% to about 2%. These mixtures will elute the following four ester components: $D_3$ (trans-3, trans-3, trans-3 tris malonic acid $C_{60}$); e,trans-3,trans-2; e,trans-4,trans-3; and $C_3$ esters. The eluted $C_3$ ester fractions are then evaporated in vacuo.

An acid miscible in the above solvent, including but not limited to p-toluenesulfonic acid monohydrate, trifluoroacetic acid (TFA) or methane sulfuric acid, is next added to a solution of the $C_3$ ester fractions in an aromatic solvent (including but not limited to toluene) to dissolve the fractions. This solution is heated to about 88-89° C. Lower temperatures can be used, but the reaction will proceed at a slower rate. If TFA is used, room temperature should be sufficient. Once the reaction has begun (after about 45 minutes, or determined via assay), additional acid should be added. A precipitate will begin forming after about 10 minutes. Heating continues until the reaction is complete (about 90 minutes or determined by assay such as TLC or HPLC). The solvent is next removed from the precipitate. Water and ethyl acetate are added to the solids to form an ethyl acetate/water mixture. The ethyl acetate solution is separated and then washed with water to remove the catalyst acid. If necessary, the ethyl acetate should be washed multiple times. The ethyl acetate is then evaporated in vacuo to leave a solid.

The solid is then dissolved in about a 1:1:2 acetonitrile:water:acetone mixture. Other ratios can be utilized to maximize solubilizing the material, including using acetone alone. The mixture is heated via an oil bath, heating mantle or the like to about 50° C., about 76.5° or about 100° C. to complete the reaction. To ensure the reaction is complete, an assay could be run. A quantity of acetone is next added to sufficiently dissolve the precipitate. Heating is continued for about 5 hours to about 7.5 hours. Any volatile solvents are then removed (for example, in vacuo) and ethyl acetate is then added to form a homogeneous solution. This solution is then evaporated in vacuo to produce a solid.

This solid is next dissolved in aromatic solvents (such as toluene or 5% t-butyl acetate in toluene (1 mg/ml)) containing methanol and water. Various ratios can be used (such as a 100:4.4:0.2); however, a limited quantity of water should be used to avoid producing two phases. This solution is then mixed well, with stirring for about an hour. After mixing, a 20 to 1 ratio of 1 M sodium hydroxide in methanol is added. After complete precipitation (once the color completely drops out which could take about one hour to about two hours), water is added. The solvent layers are then thoroughly separated, ensuring any residual solvent is removed. The aqueous layer is heated at about 60° C. to about 110° C. for about two hours plus or minus half an hour. An assay could be run to determine that the reaction is completed.

After chilling, a strong acid, such as sulfuric acid, (one that will not be extracted into ethyl acetate) is added to the solution in a quantity sufficient to neutralize the base from above. The final product is extracted with ethyl acetate as described above.

Direct Synthesis of $C_3$-Lite (in Solution or Neat).

$C_3$-lite can be directly synthesized by heating either dry or dissolved samples of $C_3$ derivatives of Hexa, Penta-1 and Penta-2. If dissolved samples are used, the derivatives should be dissolved in mixtures of acetonitrile:water. Any standard method of heating can be used, including but not limited to a heating mantel, oil bath or the like. The resulting solution/sample is heated for a sufficient time to produce $C_3$-lite (less than about 24 hours) at about 60° C. to about 70° C. to about 81° C. (the boiling point of acetonitrile). The solvents are then removed in vacuo to give a solid product.

When a neat sample of $C_3$ derivatives is utilized, the sample is heated at about 150° C. in a vacuum oven at about −30 mm Hg.

Thermal Decomposition of C_in Solution to Generate Pentas, Tetras, or $C_3$-lite.

A product comprising the Pentas, Tetras, or $C_3$-lite is produced by dissolving a sample of $C_3$ derivatives, containing Hexa, Penta-1 and Penta-2 in a 1:1 ratio of acetonitrile:water. The resulting solution is heated to about 60° C. After about 1.5 hours of heating, the Penta concentration is near its maximum. The longer heat is applied (about 3.5 to about 5.5 hours), the Penta concentration will decrease while the concentration of $C_3$-lite and Tetras will increase.

When the desired results are achieved, the solvents are removed in vacuo to give a solid product.

Utilizing NaOMe/MeOH to Synthesize a Mixture of Hexa and Penta.

Sodium methoxide or sodium hydroxide is added to a solution of e,e, e-tris dimethylmalonyl fullerene ("$C_3$ ester") in an aromatic solvent under an inert gas such as $N_2$, to form an initial solution. The aromatic solvent can be selected from the group consisting of, but not limited to, toluene and t-butyl acetate in toluene. The sodium methoxide is in a 16-20:1 ratio with the $C_3$ ester. A red-orange precipitate will begin forming immediately. After a suitable time, about 1 to 2 hours, water is added to form an aqueous and nonaqueous layer. Any color will move into the aqueous layer. The layers are then separated. The aqueous layer is chilled to 0-5° C., in an ice bath or the like, then acidified with excess sulfuric acid to a pH of about 2. This acidic solution is then extracted with ethyl acetate to transfer all of the color to the ethyl acetate extracts. The combined ethyl acetate extracts are next washed with water to remove any yellow contaminants. This solution is then evaporated and dried in vacuo at about room temperature.

Solutions for cell screening are prepared by dissolving the solid in 0.1 N sodium hydroxide. Sufficient base can be added to neutralize all carboxyls. The actual concentration can be determined by assay such as uv using 4400 for the extinction coefficient, determined on the ester precursor in toluene. HPLC protocol 1 can be used to determine percent of Hexa, Penta-1 and Penta-2. The three components can then be separated by HPLC.

The data herein demonstrate that the disclosed carboxyfullerenes are a novel class of antioxidants with the unique ability to decompose oxygen-derived free radicals, and that these compounds have unusual broad and powerful capabilities to extend the lifespan of individuals.

Further features and advantages of the above compositions and processes, as well as the structure and operation of various embodiments, are described in detail below with reference to the accompanying drawings.

The above disclosure describes several preferred embodiments which are not scope limiting in any manner. The skilled artisan in the practice of these processes and compositions will recognize other embodiments that are not overtly disclosed herein. The embodiments above are further illustrated by the examples described below. These examples are meant to illustrate these embodiments and are not to be interpreted as scope limiting in any manner.

All of the references and related art cited herein represent a portion of the present state of the art and are therefore incorporated herein in their entirety.

EXAMPLE 1

Preparation of $C_3$ Carboxyfullerenes

Materials. Silica gel (Merck grade 9385, 260-400, 60 A) was obtained from Aldrich Chemicals (St. Louis, Mo.). Other reagents were purchased from Sigma Chemical Co. (St. Louis, Mo.) and other standard sources.

The $C_3$ regioisomer of malonic acid $C_{60}$ (e,e,e $C_{60}$[C(COOH)$_2$]$_3$) was synthesized by dissolving $C_{60}$ (720 mg, 1.00 mmol) in toluene at a concentration of 1 mg/ml by stirring overnight. Dimethyl bromomalonate (632.4 mg, 2.69 mmol) was added, followed by 1,8-diazabicyclo (5.4.0) undec-7-ene (DBU, 493 mg, 3.24 mmol). The reaction mixture was stirred for 2 hours, filtered through a pad of silica gel and concentrated in vacuo. The residue was chromatographed on a 450 ml column of silica gel (Merck, 280-400 mesh), starting in toluene. The colored components were separated by adding increasing amounts of ethyl acetate (EtOAc) to the toluene. The $C_3$ fraction eluted in 5% EtOAc in toluene. Purity of the $C_{60}$ malonic ester fractions was monitored by TLC and HPLC. The $C_3$ ester (0.25 g, 0.23 mmol) was dissolved in toluene (250 ml) and sparged with nitrogen. Addition of sodium methoxide (2.22 ml of 2.2 M, 4.88 mmol) resulted in a precipitate within minutes. The mixture was stirred at room temperature under nitrogen for one hour. Water (20 ml) was added and the mixture was stirred overnight. All colored products went into the water layer. The layers were separated, and the aqueous layer was chilled and acidified with 20% sulfuric acid (1.32 ml). The solution was extracted with EtOAc three times, resulting in all color going into the organic layer. The organic layer was washed several times with water to extract a yellow contaminant. The EtOAc layer was then evaporated, and the residue 223.2 mg (89% of theoretical) was freeze-dried.

EXAMPLE 2

Experimental Method for Longevity Trial with Mice

Twelve month old C57B6NIH male and female mice (equal numbers) were purchased from the National Institute on Aging (NIA) Aging Rodent Colony. Mice shipped from this colony were not selected in any way for health, tumors or other disabilities, and all mice obtained from the colony were subsequently enrolled in the study. Mice were randomly placed in same-sex numbered cages, two per cage, ear-punched for identification, and weighed. Mice were then trained on a rotorod twice per week for three sessions, and were then tested on the rotorod in three sessions to measure motor performance at baseline. Cages were then assigned to receive either treatment A or treatment B by an observer who was blind to what these treatments would be.

Treatment A was a solution of $C_3$ (28.75 μM) in water, and treatment B was commercial food coloring added to match the red $C_3$ solution. Solution A or solution B was placed in the water bottles, and solutions were topped-off twice weekly, and filtered to remove any particulates biweekly by an individual blind to the identity of the solutions. At 19 months of age, mice were weighed again, and underwent another round of rotorod training and testing. Mice were allowed to die spontaneously, and their date of death were recorded by the Animal Housing Facility staff as part of the normal operating procedure of the facility. Facility staff believed that animals were on an antibiotic solution, and did not know the purpose of the study. When animals died, the cage number, identity of the animal, and the date of death were recorded on the death notice, which was then sent to the laboratory, where the information was entered into the database.

The results of these experiments are displayed in FIG. 4 and show a marked increase (approximately 20%) in the lifespan of mice. In addition, because longevity was increased by the oral dosing of a drug, it is the first practical method for achieving increased longevity in metazoans. The increased lifespan of $C_3$-treated mice was not accompanied by a reduction in weight.

EXAMPLE 3

Toxicity Study Utilizing Rats

Rat toxicity testing of $C_3$ was also carried out with two strains of rats (Sprague-Dawley and Long-Evans) which received up to 10 mg/kg day for 30 days without showing any toxicity (i.e., decreased survival, impaired grooming or decreased feeding).

EXAMPLES 4-13

Identified below are novel several e,e,e malonic acid/acetic acid tri-adducts of buckminsterfullerene. Major components from preparing $C_3$ Hexa include two isomeric pentacarboxylic acids in approximately equal abundance (the Penta Pair), minor products including four isomeric tetra acids (the Tetra Quartet) and four isomeric tri-decarboxylation products ($C_3$-lite). These products are less soluble in water than $C_3$ (more lipophilic) which may increase these novel compounds absorption and retention in tissues.

The processes below gives a concentration of 94+% hexacarboxylic acid and provides directed routes to the other novel components. Mixtures rich in the Penta Pair, Tetra Quartet and $C_3$-lite were obtained by decarboxylation. The Penta Pair and Tetra Quartet were also obtained via an alternative strategy using t-butyl protection.

HPLC Methods for Analysis of Derivatives

All of the following HPLC methods used a Hewlett Packard/Agilent 1100 series HPLC with a quaternary pump and diode array detector. Separations were performed on either Zorbax SB-C18 4.6×250 mm column (5 μm packing) (column A) or Zorbax SB-C8 4.6×250 mm column (5 μm packing) (column B), maintained at room temperature. All methods used a solvent flow rate of 1 ml/min.

Protocol 1—Analysis of Hexa and Penta compounds.

Solvents were 0.1% TFA in water (solvent A) and 0.1% TFA in 95% acetonitrile and 5% water (solvent B). Samples were eluted from the column using a gradient from 40:60; A:B, to 10:90; A:B, over 15 min., with an additional 15 minutes at 10:90; A:B. Compounds were monitored and identified by their UV-vis absorbance using an in-line diode array detector.

Protocol 2—Alternative method to separate Hexa and Penta compounds.

The HPLC solvents were 0.1% TFA in water (solvent A) and 0.1% TFA in 95% 2-propanol and 5% water (solvent B). Compounds were eluted from (column A or B) using a gradient from 95:5; A:B, to 52:48; A:B over 10 minutes, the gradient progressed further to 51:49; A:B over 10 minutes then to 21:79; A:B over 5 minutes. After that it remained isocratic for an additional 2 minutes.

Protocol 3—Method to separate the Tetra Quartet.

Preparations of the Tetra Quartet were eluted from (column A or B) using: 0.1% TFA in water (solvent A) and 0.1% TFA in 95% acetonitrile and 5% water (solvent B). The solvent composition was maintained at 30:70; A:B, for 35 minutes, followed by a gradient to 5:95; A:B over 2 min., followed by an additional 10 minutes at 5:95; A:B.

Protocol 4—Analysis of $C_3$-lite.

Preparations of $C_3$-lite were analyzed using solvents as described for protocol 1 with either (column A or B). The gradient was modified to start at 95:5; A:B, maintained for 5 minutes, followed by gradient change to 5:95; A:B over 30 min. The solvent composition remained at 5:95; A:B for an additional 35 min.

Protocol 5—Analysis of t-butyl, methyl esters.

The solvent was 50% acetonitrile and 50% dichloromethane (solvent A). Samples were eluted from (column A) with an isocratic program of 100% (solvent A) over 5 minutes.

Protocol 6—Analysis of partial methyl esters.

The HPLC solvent was 0.1% TFA in 95% acetonitrile and 5% water (solvent A). Samples were eluted from (column A or B) in an isocratic 100% (solvent A) solution over 120 min.

EXAMPLE 4

NaOMe/MeOH Method to Synthesize a Mixture of Hexa and Penta Isomers

Sodium methoxide (1.84 mL of 2.2M, 4.05 mmol) was added to a solution of e,e,e-tris dimethylmalonyl fullerene ($C_3$ ester) (224.1 mg, 0.202 mmol) in 224 mL of toluene under $N_2$. Precipitation of a red-orange solid began immediately. Water was added after one hour and all of the color went into the aqueous layer. The layers were separated and the aqueous layer was chilled, acidified with sulfuric acid (1.10 mL of 3.7 M, 4.07 mmol) and extracted with ethyl acetate (2×40 ml and 1×10 mL). The combined ethyl acetate extracts were washed with 3×40 mL of water which removed the yellow contaminants. Evaporation and drying in vacuo at room temperature afforded 199.2 mg (96.1% of theory based on Hexa carboxylic acid). Solutions for cell screening were prepared by dissolving the solid in 0.1 N sodium hydroxide to give a solution of approximately 25 mM by weight. The actual concentration was then determined by uv using 4400 for the extinction coefficient, determined on the ester precursor in toluene. The UV-vis λ max (nm) was 488, the max/min ratio (488/414 nm) was 2.19. Using HPLC protocol 1, it was determined that the synthesis produced 65.1% Hexa isomer, 14.3% Penta-1 and 20.6% Penta-2. The three components were separated by HPLC, and identified by mass spectrometry (Table 3) and $^1$H NMR (Table 4).

EXAMPLE 5

Toluene, 6% MeOH, and Equal Amounts of Water and NaOH to Produce 95% Hexa

A solution of water (0.216 mL, 12 mmol), methanol (17.1 mL) and $C_3$ methyl ester (667 mg, 0.601 mmol) in 500 mL of toluene was stirred for 1 h. The solution appears cloudy at first. If base is added immediately the yield of Hexa is lower. Sodium hydroxide in methanol (12.9 mL of 0.93 M, 12.0 mmol) was added. After 1.5 h, there was no ester remaining in solution, as assessed by TLC and the color of the solution. Water, 100 mL, was added. The toluene layer was separated and the aqueous layer was concentrated to remove methanol and toluene, then heated for 2 h at 60° under $N_2$ to complete the hydrolysis. Workup by extraction gave 490.8 mg (79.5% theoretical yield). The UV-vis λ max was 487 nm, and the max/min ratio (487/411 nm) was 3.10. Utilizing HPLC protocol 1, it was determined that the isomer distribution was 95.2% Hexa, 1.7% Penta-1 and 3.0% Penta-2.

EXAMPLE 6

Method Using Equal Amounts NaOH and Water, and 2% MeOH Mixed Together Before Addition, with 5% t-butyl Acetate in Toluene to Generate 88% Hexa, and the Penta Isomers Sodium hydroxide (3.679 g, 0.092 mol) was dissolved in 92 mL methanol and 1.655 mL (0.092 mol) of water to give a 0.982 M solution. A portion of this solution (12.3 mL, 12.0 mmol) was added to $C_3$ methyl ester (670 mg, 0.604 mmol) dissolved in 585 mL of toluene containing 5% t-butyl acetate (1.14 mg/mL compared to 1.0 mg/mL) at room temperature under $N_2$. A precipitate slowly formed. After 1 h, water was added to the reaction mixture. The phases were separated and the aqueous layer was concentrated to remove methanol and toluene, then heated at 60° for 2 h. The product, 573.3 mg (92.5% theoretical), was recovered from the aqueous layer by ethyl acetate extraction as described above. The UV-vis λ max was 489 nm, and the max/min ratio (489/411 nm) was 3.37. Utilizing HPLC protocol 1, it was determined that the isomer distribution was 88.4% Hexa, 5.6% Penta-1 and 6.0% Penta-2.

EXAMPLE 7

Method Using t-butyl Acetate w/5 Water Molecules to Generate 96% Hexa

A solution containing water (1.52 mL, 84.4 mmol), methanol (40 mL) and $C_3$ methyl ester (0.845 mmol by UV) in 950 mL of 5% t-butyl acetate was stirred for 30 min under $N_2$. Sodium hydroxide in methanol (16.9 mL of 1 N, 16.9 mmol) was added. After 2 h, all color was in the precipitate. Water, 50 mL, was added and the toluene was decanted and residual toluene was stripped in vacuo. The aqueous layer was heated for 2 h at 60° under $N_2$. Workup by extraction gave 798.1 mg (92.1% theoretical). The UV-vis λ max was 489 nm, and the max/min ration (489/412 nm) was 2.71. Utilizing HPLC protocol 1, it was determined that the isomer distribution was 96.7% Hexa and 1.5% of each Penta.

The total methanol concentration is 6%. If base is added immediately, or if base and all of the methanol are combined before addition to the ester, the isomer distribution shifts to lower Hexa content (see Example 6).

EXAMPLE 8

Alternative Synthesis of 97% Hexa Using Toluene Only

This procedure was the same as Example 7 except toluene was used instead of 5% t-butyl acetate in toluene. Utilizing HPLC protocol 1, it was determined that the product had an isomer distribution of 97.2% Hexa, 1.3% Penta-1 and 1.5% Penta-2. The UV-vis max was 491 nm, and the max/min ratio (491/412 nm) was 2.97, and the yield was 90.5%. $^{13}C$ NMR ($K_2CO_3$, $D_2O$, 600 MHz): δ 173.84, 173.76, 152.55, 151.33, 149.49, 149.41, 149.05, 148.98, 148.92, 148.78, 148.61, 148.13, 147.96, 146.55, 146.46, 145.89, 144.81, 143.82, 143.07, 142.99, 80.69, 79.88, 69.55.

EXAMPLE 9

Penta Pair Direct Synthesis

Step 1—Dimethyl bromomalonate (281.3 mg, 1.20 mmol) was added to di-t-butylmalonyl $C_{60}$ (0.592 mmol) in 200 mL of toluene followed by DBU (202.4 mg, 1.33 mmol) (Bingel '376 at Col. 4, lines 44-45). After 30 min, the reaction mixture was poured onto a 410 mL (4×310 cm) column of silica gel in toluene. The column was eluted with toluene until all of the bis isomers (25% by UV-vis) came off. The solvent was changed to ethyl acetate/toluene mixtures (0.5% to 2%). Ester preparations enriched in the following components eluted (using HPLC protocol 5): $D_3$ (trans-3, trans-3, trans-3 tris dimethyl malonyl $C_{60}$); e,trans-3,trans-2 tris dimethyl malonyl $C_{60}$; e,trans-4,trans-3 tris dimethyl malonyl $C_{60}$; and $C_3$. The $C_3$ ester fractions (HPLC protocol 1) were evaporated in vacuo. Mass spec. and $^1H$ NMR data are in Tables 3 and 4.

Step 2—p-Toluenesulfonic acid monohydrate (22.5 mg, 0.118 mmol) was added to a solution of the $C_3$ fractions in toluene (15 mL) and placed in an oil bath at 88-89°. After 45 min, additional p-toluenesulfonic acid monohydrate (15.6 mg, 0.082 mmol) was added. Product began precipitating within 10 min. Heating was continued for 90 min. The toluene was removed from the precipitate and water and ethyl acetate were added to the solids. The ethyl acetate was washed three times with water to remove p-toluenesulfonic acid. The ethyl acetate was evaporated in vacuo leaving 118.2 mg of solid. Compounds were analyzed using HPLC Protocol 6.

Step 3—The solid was dissolved in 10 mL of 1:1:2 acetonitrile:water:acetone. A sample, 0.2 mL, was removed for analyses. The remainder was heated in an oil bath at 76.5°. After 30 min precipitate began to separate. Acetone (10 mL) was added and the solids dissolved. Heating was continued and the decarboxylation was 73% complete after 1.75 h. After heating for a total of 7.5 h, the volatile solvents were removed in vacuo and ethyl acetate was added to give a homogeneous solution. A portion was removed for analyses (1.9 mg). The remainder was evaporated in vacuo to give 0.13 g of solid. Compounds were analyzed by HPLC protocol 1.

Step 4—The above solid (0.125 mmol) was dissolved in toluene (120 mL) containing methanol (4.9 mL) and water (0.128 mL, 7.1 mmol) and stirred for one h before addition of sodium hydroxide in methanol (2.3 mL of 1.0 M, 2.3 mmol). Solid began precipitating within 5 min. Water, 50 ml, was added after one h. The toluene was separated and the aqueous layer stripped of methanol and toluene and heated at 60° for two h. Sulfuric acid (0.621 mL of 3.7 M, 2.3 mmol) was added to the chilled solution and the product was extracted using ethyl acetate as described above. The dry weight was 91.1 mg. U-vis λ max(nm). Compounds were analyzed using HPLC protocol 1. Mass spec. and $^1$H NMR data are in Tables 3 and 4. $^{13}$C NMR($K_2CO_3$, $D_2O$, 600 MHz): δ 175.39, 175.36, 173.94, 173.88, 173.82, 173.80, 173.74, 173.68, 173.65, 153.39, 152.46, 152.32, 152.23, 152.15, 151.37, 151.22, 149.66, 149.46, 149.38, 149.24, 149.14, 149.04, 148.97, 148.86, 148.55, 148.45, 148.42, 148.36, 148.35, 148.13, 147.96, 147.78, 147.04, 146.96, 146.87, 146.70, 146.66, 146.60, 146.42, 146.38, 146.03, 145.94, 145.70, 145.55, 145.22, 144.86, 144.79, 144.67, 144.58, 144.00, 143.92, 143.88, 143.81, 143.76, 143.62, 143.07, 143.02, 142.98, 142.93, 142.11, 142.05, 80.72, 80.69, 80.58, 79.97, 79.75, 79.67, 77.21, 77.12, 76.38, 76.30, 69.52, 69.44, 69.38, 69.72.

EXAMPLE 10

Synthesis of the Tetra Quartet

Step 1—Dimethyl bromomalonate (38 mg, 0.16 mmol) was added to a sample of bis-di-t-butyl malonates of $C_{60}$ (0.167 mmol by UV) in 30 mL of toluene. DBU (28 mg, 0.18 mmol) was added and the reaction was followed by TLC (2% EtAc in toluene on silica gel). The reaction was complete after one h. The reaction mixture was poured onto a 330×2.5 cm column of silica gel in toluene. Bis fractions (12%, four components, HPLC protocol 5) were recovered in toluene and then the eluant was changed to 0.5% ethyl acetate in toluene. Fractions, including esters of $D_3$, e,trans-3,trans-2, e,trans-4,trans-3 and $C_3$ were obtained. The $C_3$ fraction was 88.5% pure by HPLC protocol 1, and was used without further purification. UV-vis (0.5% EtAc in toluene) λmax was 486 nm, the max/min ratio was 3.57.

Step 2—P-Toluenesulfonic acid hydrate (4.9 mg, 0.0258 mmol) was added to $C_3$ ester (0.0154 mmol) in 4.5 mL of toluene and the mixture was placed in an oil bath at 770. The temperature was raised to 85° over 15 min and then more p-toluenesulfonic acid(5.9 mg, 0.0310 mmol) was added. Within 5 min, precipitation began. Heating was continued for 30 min. The mixture was cooled and the toluene was decanted. Addition of water and ethyl acetate produced a two phase mixture with all of the color in the ethyl acetate layer. The ethyl acetate was washed three times with water and evaporated to give 18.3 mg of solid. Compounds were also analyzed using HPLC protocol 1.

Step 3—The solid above was dissolved in 5 mL of 4:1 acetonitrile:water and 0.546 mL was removed for analyses. The remainder was heated in an oil bath at 740. After 65 min, solids were present. Addition of 3 mL of acetone gave a homogeneous solution and heating was continued for 5.5 h. A portion, 0.8 mL, of the solution, was removed for analyses and the remainder, 7.0 mL, was concentrated to remove acetone and acetonitrile. HPLC (95:5:0.1,ACN:$H_2O$:TFA, min,%) 19.341(26.2), 38.180(25.1, 43.798(22.2), and 80.874 (21.6). Compounds were also analyzed using HPLC protocol 1.

Step 4—Sodium hydroxide, (0.59 mL Of 0.1 n, 0.059 mmol) was added to the suspension obtained above in about 3 mL of water. The solids dissolved. Sodium hydroxide (0.6 mL of 1N, 0.6 mmol) was added and the solution was heated at 62° for one h. HPLC indicated complete hydrolysis. The solution was chilled and acidified with sulfuric acid (0.162 mL of 3.7 M). Extraction with ethyl acetate afforded 11.4 mg of solid. HPLC(95:5:0.1, ACN:$H_2O$:TFA, min, %) 6.076(26.4), 10.784(24.5), 13.883(26.0), 23.589(23.1). Compounds were analyzed using HPLC protocol 1. Mass spec. and $^1$H NMR data are in Tables 3 and 4.

EXAMPLE 11

Direct Synthesis of $C_3$-Lite in Solution

A sample of $C_3$ (329.7 mg, 0.32 mmol, 71% Hexa, 15% Penta 1 and 14% Penta 2) was dissolved in 6 mL of 1:1 acetonitrile:water and placed in an oil bath at 70° C. The progress of the reaction was monitored by HPLC (Protocol 2). After 2.25 h, the reaction was nearly complete. Solids began precipitating after 5 h. Heating was continued for 24 h. Solvents were removed in vacuo to give 199.3 mg of product which had the following composition by HPLC protocol 1: $C_3$-lite peak 1 (14.0%), peak 2 (39.4%), peak 3 (37.0%), peak 4 (8.7%). LC-MS pos m/e was 895 for each, neg m/e was 1007 for each (M+TFA-H). All had the UV-vis spectrum of $C_3$ (e,e,e additions to $C_{60}$). $^1$H NMR and mass spec data are in Tables 3 and 4 The solid was soluble in sodium hydroxide, moderately soluble in acetone and ethyl acetate, poorly soluble in water, methanol and acetonitrile.

EXAMPLE 12

Thermal Decomposition of $C_3$ in Solution to Generate Pentas, Tetras, or $C_3$-Lite A sample of $C_3$ containing 97.4% Hexa, 1.2% Penta 1 and 1.3% Penta 2 (74.8 mg) was dissolved in 10 mL of 1:1 acetonitrile:water and heated at 60° C. The composition was monitored by HPLC, using protocols 2 and 4 (see Table 1).

TABLE 1

HPLC analysis of products produced by thermal decomposition of $C_3$ in solution.

| Identification | Retention Times (min) | Incubation Time, h | | | |
| --- | --- | --- | --- | --- | --- |
| | | 0 | 1.5 | 3.5 | 5.5 |
| Hexa | 10.8 | **97.4% | 40.5 | 9.2 | 2.6 |
| Penta 1 | 13.0 | 1.2 | 23.1 | 20.7 | 13.7 |
| Tetra | 15.6 | — | 3.5 | 9.5 | 12.2 |
| Tris | 18.9 | — | — | 1.3 | 2.6 |
| Penta 2 | 19.3 | 1.3 | 23.7 | 24.0 | 17.9 |
| Tetra | 22.1 | — | 3.1 | 9.0 | 12.0 |
| Tetra | 26.2 | — | 3.4 | 10.6 | 14.0 |
| Tetra | 32.0 | — | 2.8 | 2.9 | 6.6 |
| Tris | 39.0 | — | — | 9.2 | 13.4 |
| Tris | 56.9 | — | — | 2.3 | 4.4 |

TABLE 1-continued

HPLC analysis of products produced by thermal decomposition of $C_3$ in solution.

| Identification | Retention Times (min) | Incubation Time, h | | | |
|---|---|---|---|---|---|
| | | 0 | 1.5 | 3.5 | 5.5 |
| Tris | 73.9* | — | — | — | — |
| Sums | Hexa | | 40.5 | 9.2 | 2.6 |
| | Pentas | | 46.8 | 44.7 | 31.6 |
| | Tetras | | 12.8 | 38.3 | 51.6 |
| | Tris | | — | 6.5 | 13.6 |

*not obtained.
**All values are percent of injected compound.

EXAMPLE 13

Neat Decarboxylation of $C_3$ to $C_3$-Lite

A sample of $C_3$ containing 93.8% Hexa, 3.5% Penta 1 and 2.7% Penta 2 was placed as a dry powder in a vacuum oven at 150° C. and −30 mm of Hg. The composition was monitored by HPLC protocol 2. Table 2 shows the time-dependent production of decarboxylation products of $C_3$, including $C_3$-lite (See Table 2).

TABLE 2

HPLC analysis of products produced by neat thermal decomposition of $C_3$.

| Identification | Retention Time (min) | Incubation Time, h | | | |
|---|---|---|---|---|---|
| | | 0 | 19 | 64 | 168 |
| Hexa | 28.9 | **93.8% | — | — | — |
| Penta-1 | 30.2 | 3.5 | — | — | — |
| Tetra-1 | 31.9 | — | — | — | — |
| Penta-2 | 33.2 | 2.7 | — | — | — |
| Tris-1 | 34.1 | — | 13.2 | 13.1 | 13.0 |
| Tetra-2 | 34.4 | — | — | — | — |
| Tetra-3 | 35.5 | — | — | — | — |
| Tris-2 | 37.0 | — | 36.5 | 36.6 | 36.6 |
| Tetra-4 | 37.5 | — | — | — | — |
| Tris-3 | 39.9 | — | 37.0 | 37.0 | 37.1 |
| Tris-4 | 43.4 | — | 13.4 | 13.2 | 13.3 |
| Sums | Hexa | 93.8 | — | — | — |
| | Penta pair | 6.2 | — | — | — |
| | Tetra Quarter | — | — | — | — |
| | $C_3$-lite | — | 100 | 100 | 100 |

**All values are percent of injected compound.

TABLE 3

Mass Spectral Data. Compound numbers refer to those listed above.

| Compound | Mass spec | M/e, expected | M/e found | Base peak | Fragment |
|---|---|---|---|---|---|
| 1 | QTOF ES- | 1025 | 1025 | 1025 | |
| 2 | " | 981 | 981 | 981 | $M-2CO_2/2$ |
| 3 | " | 937 | 937 | 893 | $-CO_2$ |
| 4 | " | 893 | 893 | 893 | |
| 5 | FAB+ | 1195 | 1195 | 720 | $C(CO_2Me)_2$ |
| 6 | " | 1279 | 1279 | 720 | |
| 7 | QTOF ES- | 1081 | 1081 | 1038 | $-CO_2$ |
| 8 | " | 1053 | 1053 | 1009 | $-CO_2$ |
| 9 | " | 1037 | 1037 | 1037 | |
| 10 | " | 965 | 965 | 965 | |

TABLE 4

$^1$H NMR Data[1]

| Compound | Solvent | δCH[2] | δCH | δMethyl | δt-Butyl |
|---|---|---|---|---|---|
| 2 | DMSO-$d_6$ | 4.894(0.53) | 4.750}0.46) 4.734 | — | — |
| 3 | " | 4.887(0.47) 4.870 | 4.739(0.53) 4.721 | — | — |
| 4 | " | 4.881(0.56) 4.863 4.861 | 4.730(0.44) 4.726 4.711 4.707 | — | — |
| 5 | CDCl$_3$ | — | — | 3.875(4) 3.832(2) 3.824(2) | 1.505(3) 1.487(6) 1.475(3) |
| 6 | " | — | — | 3.872(1) 3.829(1) | 1.503(3) 1.491(3) 1.487(3) 1.473(3) |
| 7 | Acetone-$d_6$ | | | 3.949(1) 3.889(1) | |
| 8 | Acetone-$d_6$ | | | 3.948(1) 3.887(1) | |
| 9 | DMSO-$d_6$ | 4.838(1) | 4.676(1) | 3.902(6) 3.843(6) | |
| 10 | " | 4.806(1) | 4.658(1) | 3.896(3) 3.885 3.836(3) 3.829 | |

[1]Varian Unity 300 NMR Spectrometer
[2]Chemical shift(integration)

TABLE 5

Carbon-Hydrogen analysis
Combustion Analysis

| Compound | | Calculated | | Found | |
|---|---|---|---|---|---|
| | | C | H | C | H |
| Hexa $C_3$ (run 1) | $C_{69}H_6O_{12} \times 3H_2O$ | 76.68 | 1.12 | 76.88 73.55 | 1.76 1.73 |
| Hexa $C_3$ (run 2) | $C_{69}H_6O_{12} \times 4H_2O$* | 75.42 | 1.28 | 75.15 74.99 | 1.96 1.94 |
| $C_3$ lite | $C_{66}H_6O_6 \times 2.5H_2O$ | 84.35 | 1.18 | 84.78 | 1.18 |

*7.41% wt loss on drying

TABLE 6

Chemical properties of $C_3$ and $C_3$-lite

| Compound | Acidity[1] [H+/A−] | Thermal Stability[2] $t_{1/2}$ min, 60° | # of products | Solubility[3] Water, mg/ml | Sodium salt[5] | Hydration of Na salt[4] |
|---|---|---|---|---|---|---|
| $C_3$ | 3.3 | 60 | 10 | >454[6] | >450[6] | 1.31 |
| $C_3$ lite | — | — | — | insoluble | 9 | 4.36 |

[1] Measured pH and uv in 1:1 acetonitrile:water. All solutions were 1.29-1.97 × 10-4 mmol/mL.
[2] In 1:1 acetonitrile:water.
[3] The concentration was calculated from the uv spectrum measured on the liquid portion of a saturated solution.
[4] Sodium salts were freeze dried at room temperature for 4 days. This value in the dry weight divided by the expected weight for complete neutralization.
[5] Calculated for the acid.
[6] Solution too dark to see undissolved solids.

TABLE 7

Visible spectroscopic properties[1]

| Compound | | Ester[2] Solution | | | HPLC | | Acid[3] Solution | | HPLC | | Literature values[4] | |
|---|---|---|---|---|---|---|---|---|---|---|---|---|
| | | λ nm | ε | εmin | λ nm | εmin | λ nm | εmin | λ nm | εmin | λ nm | ε |
| $C_3$ | max | 485 | 4400 | 4.55 | 482 | 4.85 | 487 | 3.7 | 484 | 5.08 | 481[5] | 4000 |
| | min | 409 | 967 | | 408 | | 409 | | 408 | | 486[6] | 3270 |

[1] Solution spectra measured on Beckman DU-600 in 1 cm cells. HPLC values from Agilent diode array detector in acetonitrile:water: 0.1 TFA gradients.
[2] Measured on methyl esters in toluene
[3] Measured on half neutralized acids in water
[4] Dichloromethane, no data given for minima
[5] U. Reuther, T. Brandmuller, W. Donaubauer, F. Hampel, A. Hirsch, Chem. Eur. J. 2002, 2261-2273
[6] G. Rapenne, J. Crassous, L. E. Echegoyen, L. Echegoyen, E. Flapan, F. Diederich, Helv. Chim. Acta. 2000, 83, 1209-1223

In view of the foregoing, it will be seen that the several advantages of the above embodiments and examples are achieved and attained. The embodiments were chosen and described in order to best explain the principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting. For example, the process as described above could easily be applied to other metazoans, including but not limited to humans, with the same results. Thus, the breadth and scope of the present invention should not be limited by any of the above-described exemplary embodiments, but should be defined only in accordance with the following claims appended hereto and their equivalents.

What is claimed is:

1. A method of inhibiting neurotoxic injury in a patient wherein said injury is caused by free radical oxygen species released by neurons due to the stimulation by glutamate of NMDA receptors of said neurons that comprises administering to said patient a composition comprising an e,e,e malonic acid/acetic acid tri-adduct of buckminsterfullerene of the formula $C_{60}(R)_3$ represented by the following structure:

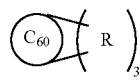

wherein each R is independently selected from the group consisting of moieties of the formula $=CR^1R^2$, wherein each $R^1$ and $R^2$ of said $=CR^1R^2$ moiety is independently selected from the group consisting of —H and —COOH, provided, however, that at least one $R^1$ or $R^2$ of at least one of said $=CR^1R^2$ moieties is a hydrogen, and wherein the C in each of said $=CR^1R^2$ moieties is bonded directly to two adjacent carbons of the $C_{60}$ moiety; or a pharmaceutically acceptable salt of said e,e,e malonic acid/acetic acid tri-adduct of buckminsterfullerene or pharmaceutically acceptable ester of said e,e,e malonic acid/acetic acid tri-adduct of buckminsterfullerene, and a pharmaceutically acceptable carrier, wherein said buckminsterfullerene, said salt, or said ester, is present in said composition in an amount effective to inhibit said neurotoxic injury.

2. The method of claim 1 wherein the e,e,e malonic acid/acetic acid tri-adduct of buckminsterfullerene is selected from the group consisting of $C_{60}(C(COOH)_2)_2(CHCOOH)$, $C_{60}(C(COOH)_2)(CHCOOH)_2$, and $C_{60}(CHCOOH)_3$.

3. The method of claim 1 wherein said e,e,e malonic acid/acetic acid tri-adduct of buckminsterfullerene is administered in an amount from about 1.5 mg/kg to about 1500 mg/kg daily.

4. The method of claim 3 wherein said e,e,e malonic acid/acetic acid tri-adduct of buckminsterfullerene is administered in an amount from about 10 mg/kg to about 60 mg/kg daily.

5. The method of claim 3 wherein said e,e,e malonic acid/acetic acid tri-adduct of buckminsterfullerene is administered orally.

6. The method of claim 3 wherein said e,e,e malonic acid/acetic acid tri-adduct of buckminsterfullerene is administered intravenously.

7. The method of claim 3 wherein said e,e,e malonic acid/acetic acid tri-adduct of buckminsterfullerene is $C_{60}(CHCOOH)_3$.

* * * * *